(12) United States Patent
Ackerman et al.

(10) Patent No.: US 7,572,586 B2
(45) Date of Patent: Aug. 11, 2009

(54) IDENTIFYING SUSCEPTIBILITY TO CARDIAC HYPERTROPHY

(75) Inventors: Michael J. Ackerman, Rochester, MN (US); Sara Van Driest, Nashville, TN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 195 days.

(21) Appl. No.: 11/555,548

(22) Filed: Nov. 1, 2006

(65) Prior Publication Data

US 2007/0207473 A1    Sep. 6, 2007

Related U.S. Application Data

(60) Provisional application No. 60/732,776, filed on Nov. 1, 2005.

(51) Int. Cl.
*C12Q 1/68* (2006.01)
*C12P 19/34* (2006.01)

(52) U.S. Cl. ............... 435/6; 435/91.2; 536/24.3

(58) Field of Classification Search .......... 435/6, 435/91.2; 536/24.3
See application file for complete search history.

(56) References Cited

U.S. PATENT DOCUMENTS

| | | | | |
|---|---|---|---|---|
| 5,382,510 | A * | 1/1995 | Levine et al. ............... | 435/6 |
| 5,648,482 | A * | 7/1997 | Meyer ...................... | 536/24.33 |
| 2002/0127548 | A1 * | 9/2002 | Siedman et al. ............ | 435/6 |

FOREIGN PATENT DOCUMENTS

WO    WO 99/57318    11/1999

OTHER PUBLICATIONS

Andersen et al., European Journal of Human Genetics 12(8), 673-677 (Aug. 2004).*
Erdmann et al., Clinical Genetics 64(4), 339-349 (2003).*
Morner et al., Journal of Molecular and Cellular Cardiology 35(7), 841-849 (2003).*
GenBank Accession No. NM_000256, dated Jun. 26, 2007, 8 pages.
GenBank Accession No. NM_007078, dated Jul. 30, 2007, 6 pages.
Ackerman et al., "A Novel Mutation in KVLQT1 Is the Molecular Basis of Inherited Long QT Syndrome in a Near-Drowning Patient's Family," *Pediatr. Res.*, 1998, 44:148-153.
Jääskeläinen et al., "Mutations in the cardiac myosin-binding protein C gene are the predominant cause of familial hypertrophic cardiomyopathy in eastern Finland," *J. Mol. Med.*, 2002, 80:412-422.
Lamke et al., "Surgical pathology of subaortic septal myectomy associated with hypertrophic cardiomyopathy: A study of 204 cases (1996-2000)," *Cardiovasc. Pathol.*, 2003, 12:149-158.
Prince et al., "Robust and accurate single nucleotide polymorphism genotyping by dynamic allele-specific hybridization (DASH): design criteria and assay validation," *Genome Res.*, 2001, 11(1):152-162.
Rost et al., "The PredictProtein server," *Nucl. Acids Res.*, 2004, 32:W321-326.
Schafer et al., "DNA variation and the future of human genetics," *Nat. Biotechnol.*, 1998, 15:33-39.
Stoneking et al., "Population variation of human mtDNA control region sequences detected by enzymatic amplification and sequence-specific oligonucleotide probes," *Am. J. Hum. Genet.*, 1991, 48:370-382.
Underhill et al., "Detection of numerous Y chromosome biallelic polymorphisms by denaturing high-performance liquid chromatography," *Genome Res.*, 1997, 7:996-1005.
Van Driest et al., "Myosin Binding Protein C Mutations and Compound Heterozygosity in Hypertrophic Cardiomyopathy," *J. Am. Coll. Cardiol.*, 2004, 44:1903-1910.
Van Driest et al., "Comprehensive Analysis of the Beta-Myosin Heavy Chain Gene in 389 Unrelated Patients With Hypertrophic Cardiomyopathy," *J. Am. Coll. Cardiol.*, 2004, 44:602-610.
Vatta et al., "Mutations in *Cypher/ZASP* in Patients With Dilated Cardiomyopathy and Left Ventricular Non-Compaction," *J. Am. Coll. Cardiol.*, 2003, 42(11):2014-2027.

* cited by examiner

*Primary Examiner*—Kenneth R. Horlick
(74) *Attorney, Agent, or Firm*—Fish & Richardson P.C.

(57) ABSTRACT

This document provides methods and materials related to identifying, assessing, and predicting hypertrophic cardiomyopathy (HCM) in mammals. For example, methods and materials for using mutations (e.g., mutations in ZASP and MYBPC3 nucleic acids) to identify, assess, and predict HCM in mammals (e.g., humans) are provided.

12 Claims, 14 Drawing Sheets

C.

Case 7

| | | |
|---|---|---|
| Homo sapiens | ...YEQFFA | L LCAKCNT... |
| Mus musculus | ...YEQFFA | P LCAKCNT... |
| Rattus norvegicus | ...YEQFFA | P ICAKCNT... |
| Gallus gallus | ...YEQFFA | P ICAKCNT... |
| Danio rerio | ...YEQFFA | P TCSRCHT... |
| Drosophila melanogaster | ...YEEFFA | P TCARCST... |
| | ...FEKYLA | P TCSKCAG... |

D.

LIM Domain 1

$N_{557}$ LCGHCNNVIRGPFLVAMGRSWHPEEFTCAYCKTSLADVCFVEEQNNVYCERCYEQFFA
       EE EEEE HHHHHHHH EEEEE HHHHHHHH EEEEE

HHHHHH HHHHHHHH HHHHH

LCGHCNNVIRGPFLVAMGRSWHPEEFTCAYCKTSLADVCFVEEQNNVYCERCYEQFFA

LIM Domain 2 $C_{639}$

P LCAKCNTKIMGEVMHALRQTWHTT
H HHHH HHHHHHHHH HHH

L LCAKCNTKIMGEVMHALRQTWHTT
   HHHHHHHH

Nucleic acid and amino acid sequence for ZASP 'short isoform'

```
GCAGGCGGAGTGCCTGAGTGCCCTCTCACTCAACCCTCTCTACCCTTTGTCTGCAGAGGC
............................................................

GGCCGCTGACAGCACCAGCATGTCTTACAGTGTGACCCTGACTGGGCCCGGGCCCTGGGG
.....................-M--S--Y--S--V--T--L--T--G--P--G--P--W--G

CTTCCGTCTGCAGGGGGGCAAGGACTTCAACATGCCCCTCACTATCTCCCGGATCACACC
--F--R--L--Q--G--G--K--D--F--N--M--P--L--T--I--S--R--I--T--P

AGGCAGCAAGGCAGCCCAGTCCCAGCTCAGCCAGGGTGACCTCGTGGTGGCCATTGACGG
--G--S--K--A--A--Q--S--Q--L--S--Q--G--D--L--V--V--A--I--D--G

CGTCAACACAGACACCATGACCCACCTGGAAGCCCAGAACAAGATCAAGTCTGCCAGCTA
--V--N--T--D--T--M--T--H--L--E--A--Q--N--K--I--K--S--A--S--Y

CAACTTGAGCCTCACCCTGCAGAAATCAAAGCGTCCCATTCCCATCTCCACGACAGCACC
--N--L--S--L--T--L--Q--K--S--K--R--P--I--P--I--S--T--T--A--P

TCCAGTCCAGACCCCTCTGCCGGTGATCCCTCACCAGAAGGTAGCCAGCCCCGAGCCCAT
--P--V--Q--T--P--L--P--V--I--P--H--Q--K--V--A--S--P--E--P--M

GAGCGCCGACTACCAGGAACGCTTCAACCCCAGTGCCCTGAAGGACTCGGCCCTGTCCAC
--S--A--D--Y--Q--E--R--F--N--P--S--A--L--K--D--S--A--L--S--T

CCACAAGCCCATCGAGGTGAAGGGGCTGGGCGGCAAGGCCACCATCATCCATGCGCAGTA
--H--K--P--I--E--V--K--G--L--G--G--K--A--T--I--I--H--A--Q--Y

CAACACGCCCATCAGCATGTATTCCCAGGATGCCATCATGGATGCCATCGCTGGGCAGGC
--N--T--P--I--S--M--Y--S--Q--D--A--I--M--D--A--I--A--G--Q--A

CCAAGCCCAAGGCAGTGACTTCAGTGGGAGCCTCCCTATTAAGGACCTTGCCGTAGACAG
--Q--A--Q--G--S--D--F--S--G--S--L--P--I--K--D--L--A--V--D--S

CGCCTCTCCCGTCTACCAGGCTGTGATTAAGAGCCAGAACAAGCCAGAAGATGAGGCTGA
--A--S--P--V--Y--Q--A--V--I--K--S--Q--N--K--P--E--D--E--A--D

CGAGTGGGCACGCCGTTCCTCCAACCTGCAGTCTCGCTCCTTCCGCATCCTGGCCCAGAT
--E--W--A--R--R--S--S--N--L--Q--S--R--S--F--R--I--L--A--Q--M

GACGGGGACAGAATTCATGCAAGACCCTGATGAAGAAGCTCTGCGAAGGTCAAGGGAAAG
--T--G--T--E--F--M--Q--D--P--D--E--E--A--L--R--R--S--R--E--R

GTTTGAAACGGAACGTAACAGCCCACGTTTTGCCAAATTGCGCAACTGGCACCATGGCCT
--F--E--T--E--R--N--S--P--R--F--A--K--L--R--N--W--H--H--G--L

TTCAGCCCAAATCCTTAATGTTAAAAGCTAAAAGGCTGCCTGGAATCCCCCCACCCCAAC
--S--A--Q--I--L--N--V--K--S--*-............................

AGGCTGGACTCCCTCCATCCTTACCCCCACACAGATCTGGCATGTGAGCCCCACGGTGAT
............................................................
```

Figure 8 (continued)

Nucleic acid and amino acid sequence for ZASP 'long isoform'

```
GCGGCCGCTGACAGCACCAGCATGTCTTACAGTGTGACCCTGACTGGGCCCGGGCCCTGG
....................-M--S--Y--S--V--T--L--T--G--P--G--P--W-

GGCTTCCGTCTGCAGGGGGGCAAGGACTTCAACATGCCCCTCACTATCTCCCGGATCACA
-G--F--R--L--Q--G--G--K--D--F--N--M--P--L--T--I--S--R--I--T-

CCAGGCAGCAAGGCAGCCCAGTCCCAGCTCAGCCAGGGTGACCTCGTGGTGGCCATTGAC
-P--G--S--K--A--A--Q--S--Q--L--S--Q--G--D--L--V--V--A--I--D-

GGCGTCAACACAGACACCATGACCCACCTGGAAGCCCAGAACAAGATCAAGTCTGCCAGC
-G--V--N--T--D--T--M--T--H--L--E--A--Q--N--K--I--K--S--A--S-

TACAACTTGAGCCTCACCCTGCAGAAATCAAAGCGTCCCATTCCCATCTCCACGACAGCA
-Y--N--L--S--L--T--L--Q--K--S--K--R--P--I--P--I--S--T--T--A-

CCTCCAGTCCAGACCCCTCTGCCGGTGATCCCTCACCAGAAGGACCCCGCTCTGGACACG
-P--P--V--Q--T--P--L--P--V--I--P--H--Q--K--D--P--A--L--D--T-

AACGGCAGCCTGGTGGCACCCAGCCCCAGCCCTGAGGCGAGGGCCAGCCCAGGCACCCCA
-N--G--S--L--V--A--P--S--P--S--P--E--A--R--A--S--P--G--T--P-

GGCACCCCGGAGCTCAGGCCCACCTTTAGCCCTGCCTTCTCCCGGCCCTCCGCCTTCTCC
-G--T--P--E--L--R--P--T--F--S--P--A--F--S--R--P--S--A--F--S-

TCACTCGCCGAGGCCTCTGACCCTGGCCCTCCGCGGGCCAGCCTGAGGGCCAAGACCAGC
-S--L--A--E--A--S--D--P--G--P--P--R--A--S--L--R--A--K--T--S-

CCAGAGGGGGCCCGGGACCTACTCGGCCCAAAAGCCCTGCCGGGCTCGAGCCAGCCGAGG
-P--E--G--A--R--D--L--L--G--P--K--A--L--P--G--S--S--Q--P--R-

CAATATAACAACCCCATTGGCCTGTACTCGGCAGAGACCCTGAGGGAGATGGCTCAGATG
-Q--Y--N--N--P--I--G--L--Y--S--A--E--T--L--R--E--M--A--Q--M-

TACCAGATGAGCCTCCGAGGGAAGGCCTCGGGTGTCGGACTCCCAGGAGGGAGCCTCCCT
-Y--Q--M--S--L--R--G--K--A--S--G--V--G--L--P--G--G--S--L--P-

ATTAAGGACCTTGCCGTAGACAGCGCCTCTCCCGTCTACCAGGCTGTGATTAAGAGCCAG
-I--K--D--L--A--V--D--S--A--S--P--V--Y--Q--A--V--I--K--S--Q-

AACAAGCCAGAAGATGAGGCTGACGAGTGGGCACGCCGTTCCTCCAACCTGCAGTCTCGC
-N--K--P--E--D--E--A--D--E--W--A--R--R--S--S--N--L--Q--S--R-

TCCTTCCGCATCCTGGCCCAGATGACGGGGACAGAATTCATGCAAGACCCTGATGAAGAA
-S--F--R--I--L--A--Q--M--T--G--T--E--F--M--Q--D--P--D--E--E-

GCTCTGCGAAGGTCAAGCACCCCTATTGAGCATGCGCCGGTGTGCACCAGCCAGGCCACC
-A--L--R--R--S--S--T--P--I--E--H--A--P--V--C--T--S--Q--A--T-

ACCCCGCTGCTGCCCGCTTCTGCCCAGCCACCTGCTGCTGCCTCTCCCAGTGCGGCTTCG
-T--P--L--L--P--A--S--A--Q--P--P--A--A--A--S--P--S--A--A--S-

CCACCCCTGGCCACAGCTGCTGCCCACACTGCCATCGCCTCCGCCTCCACCACAGCCCCT
-P--P--L--A--T--A--A--A--H--T--A--I--A--S--A--S--T--T--A--P-

GCTTCAAGTCCTGCCGACAGCCCAAGGCCCCAGGCCTCTTCCTACAGCCCCGCAGTGGCC
-A--S--S--P--A--D--S--P--R--P--Q--A--S--S--Y--S--P--A--V--A-
```

Figure 8 (continued)

```
GCCTCTTCAGCACCTGCCACCCACACCAGCTACAGTGAGGGCCCCGCCGCCCCTGCACCC
-A--S--S--A--P--A--T--H--T--S--Y--S--E--G--P--A--A--P--A--P-

AAGCCCCGGGTTGTCACCACTGCCAGCATCCGGCCTTCTGTCTACCAGCCAGTGCCTGCA
-K--P--R--V--V--T--T--A--S--I--R--P--S--V--Y--Q--P--V--P--A-

TCTACCTACAGCCCGTCCCCAGGGGCCAATTACAGTCCCACTCCCTACACCCCCTCCCCT
-S--T--Y--S--P--S--P--G--A--N--Y--S--P--T--P--Y--T--P--S--P-

GCCCCTGCCTACACCCCCTCCCCTGCCCCTGCCTACACCCCCTCACCTGTCCCCACCTAC
-A--P--A--Y--T--P--S--P--A--P--A--Y--T--P--S--P--V--P--T--Y-

ACTCCATCCCCAGCACCAGCCTATACCCCCTCACCTGCCCCCAACTATAACCCTGCACCC
-T--P--S--P--A--P--A--Y--T--P--S--P--A--P--N--Y--N--P--A--P-

TCGGTGGCCTACAGCGGGGGCCCTGCGGAGCCTGCCAGCCGTCCACCCTGGGTGACAGAT
-S--V--A--Y--S--G--G--P--A--E--P--A--S--R--P--P--W--V--T--D-

GATAGCTTCTCCCAGAAGTTTGCCCCGGGCAAGAGCACCACCTCCATCAGCAAGCAGACC
-D--S--F--S--Q--K--F--A--P--G--K--S--T--T--S--I--S--K--Q--T-

CTGCCCCGGGGAGGCCCAGCCTACACCCCAGCGGGTCCTCAGGTGCCACCACTTGCCAGG
-L--P--R--G--G--P--A--Y--T--P--A--G--P--Q--V--P--P--L--A--R-

GGGACCGTCCAGAGGGCTGAGCGATTCCCAGCCAGCAGCCGGACTCCACTCTGCGGTCAC
-G--T--V--Q--R--A--E--R--F--P--A--S--S--R--T--P--L--C--G--H-

TGCAACAATGTCATCCGGGGCCCATTTCTGGTAGCCATGGGCCGTTCTTGGCACCCTGAA
-C--N--N--V--I--R--G--P--F--L--V--A--M--G--R--S--W--H--P--E-

GAGTTCACCTGTGCCTACTGCAAGACTTCCCTGGCAGATGTGTGCTTTGTGGAAGAGCAG
-E--F--T--C--A--Y--C--K--T--S--L--A--D--V--C--F--V--E--E--Q-

AACAACGTTTACTGTGAGCGATGTTATGAGCAATTCTTTGCCCCGCTGTGTGCCAAGTGC
-N--N--V--Y--C--E--R--C--Y--E--Q--F--F--A--P--L--C--A--K--C-

AACACCAAAATTATGGGGGAAGTAATGCATGCCTTGAGACAGACATGGCACACCACCTGC
-N--T--K--I--M--G--E--V--M--H--A--L--R--Q--T--W--H--T--T--C-

TTCGTCTGTGCGGCCTGCAAGAAGCCTTTTGGGAACAGCCTCTTCCACATGGAAGACGGG
-F--V--C--A--A--C--K--K--P--F--G--N--S--L--F--H--M--E--D--G-

GAGCCCTACTGCGAGAAGACTACATCAATCTGTTCAGCACCAAGTGCCATGGCTGCGAT
-E--P--Y--C--E--K--D--Y--I--N--L--F--S--T--K--C--H--G--C--D-

TTCCCCGTGGAGGCTGGCGACAAGTTTATCGAAGCCCTGGGCCACACTTGGCACGACACC
-F--P--V--E--A--G--D--K--F--I--E--A--L--G--H--T--W--H--D--T-

TGCTTCATTTGCGCAGTCTGCCATGTGAATCTGGAGGGGCAGCCGTTCTACTCCAAGAAG
-C--F--I--C--A--V--C--H--V--N--L--E--G--Q--P--F--Y--S--K--K-

GACAGACCCCTGTGCAAGAAGCACGCACACACCATCAACTTGTAGGCGGCCAAGGCCGCC
-D--R--P--L--C--K--K--H--A--H--T--I--N--L--*................
```

Figure 9

Nucleic acid and amino acid sequence for *MYBPC3*

```
         CCTGCTTCGTGCCTGGTGTGACGTCTCTCAGGATGCCTGAGCCGGGGAAGAAGCCAGTCT
.............................-M--P--E--P--G--K--K--P--V--

CAGCTTTTAGCAAGAAGCCACGGTCAGTGGAAGTGGCCGCAGGCAGCCCTGCCGTGTTCG
S--A--F--S--K--K--P--R--S--V--E--V--A--A--G--S--P--A--V--F--

AGGCCGAGACAGAGCGGGCAGGAGTGAAGGTGCGCTGGCAGCGCGGAGGCAGTGACATCA
E--A--E--T--E--R--A--G--V--K--V--R--W--Q--R--G--G--S--D--I--

GCGCCAGCAACAAGTACGGCCTGGCCACAGAGGGCACACGGCATACGCTGACAGTGCGGG
S--A--S--N--K--Y--G--L--A--T--E--G--T--R--H--T--L--T--V--R--

AAGTGGGCCCTGCCGACCAGGGATCTTACGCAGTCATTGCTGGCTCCTCCAAGGTCAAGT
E--V--G--P--A--D--Q--G--S--Y--A--V--I--A--G--S--S--K--V--K--

TCGACCTCAAGGTCATAGAGGCAGAGAAGGCAGAGCCCATGCTGGCCCCTGCCCCTGCCC
F--D--L--K--V--I--E--A--E--K--A--E--P--M--L--A--P--A--P--A--

CTGCTGAGGCCACTGGAGCCCCTGGAGAAGCCCCGGCCCCAGCCGCTGAGCTGGGAGAAA
P--A--E--A--T--G--A--P--G--E--A--P--A--P--A--A--E--L--G--E--

GTGCCCCAAGTCCCAAAGGGTCAAGCTCAGCAGCTCTCAATGGTCCTACCCCTGGAGCCC
S--A--P--S--P--K--G--S--S--S--A--A--L--N--G--P--T--P--G--A--

CCGATGACCCCATTGGCCTCTTCGTGATGCGGCCACAGGATGGCGAGGTGACCGTGGGTG
P--D--D--P--I--G--L--F--V--M--R--P--Q--D--G--E--V--T--V--G--

GCAGCATCACCTTCTCAGCCCGCGTGGCCGGCGCCAGCCTCCTGAAGCCGCCTGTGGTCA
G--S--I--T--F--S--A--R--V--A--G--A--S--L--L--K--P--P--V--V--

AGTGGTTCAAGGGCAAATGGGTGGACCTGAGCAGCAAGGTGGGCCAGCACCTGCAGCTGC
K--W--F--K--G--K--W--V--D--L--S--S--K--V--G--Q--H--L--Q--L--

ACGACAGCTACGACCGCGCCAGCAAGGTCTATCTGTTCGAGCTGCACATCACCGATGCCC
H--D--S--Y--D--R--A--S--K--V--Y--L--F--E--L--H--I--T--D--A--

AGCCTGCCTTCACTGGCAGCTACCGCTGTGAGGTGTCCACCAAGGACAAATTTGACTGCT
Q--P--A--F--T--G--S--Y--R--C--E--V--S--T--K--D--K--F--D--C--

CCAACTTCAATCTCACTGTCCACGAGGCCATGGGCACCGGAGACCTGGACCTCCTATCAG
S--N--F--N--L--T--V--H--E--A--M--G--T--G--D--L--D--L--L--S--

CCTTCCGCCGCACGAGCCTGGCTGGAGGTGGTCGGCGGATCAGTGATAGCCATGAGGACA
A--F--R--R--T--S--L--A--G--G--G--R--R--I--S--D--S--H--E--D--

CTGGGATTCTGGACTTCAGCTCACTGCTGAAAAAGAGCAGCAGTTTCCGGACCCCGAGGG
T--G--I--L--D--F--S--S--L--L--K--K--S--S--S--F--R--T--P--R--

ACTCGAAGCTGGAGGCACCAGCAGAGGAGGACGTGTGGGAGATCCTACGGCAGGCACCCC
D--S--K--L--E--A--P--A--E--E--D--V--W--E--I--L--R--Q--A--P--

CATCTGAGTACGAGCGCATCGCCTTCCAGTACGGCGTCACTGACCTGCGCGGCATGCTAA
P--S--E--Y--E--R--I--A--F--Q--Y--G--V--T--D--L--R--G--M--L--

AGAGGCTCAAGGGCATGAGGCGCGATGAGAAGAAGAGCACAGCCTTTCAGAAGAAGCTGG
K--R--L--K--G--M--R--R--D--E--K--K--S--T--A--F--Q--K--K--L--
```

Figure 9 (Continued)

```
AGCCGGCCTACCAGGTGAGCAAAGGCCACAAGATCCGGCTGACCGTGGAACTGGCTGACC
E--P--A--Y--Q--V--S--K--G--H--K--I--R--L--T--V--E--L--A--D--

ATGACGCTGAGGTCAAATGGCTCAAGAATGGCCAGGAGATCCAGATGAGCGGCAGGTACA
H--D--A--E--V--K--W--L--K--N--G--Q--E--I--Q--M--S--G--R--Y--

TCTTTGAGTCCATCGGTGCCAAGCGTACCCTGACCATCAGCCAGTGCTCATTGGCGGACG
I--F--E--S--I--G--A--K--R--T--L--T--I--S--Q--C--S--L--A--D--

ACGCAGCCTACCAGTGCGTGGTGGGTGGCGAGAAGTGTAGCACGGAGCTCTTTGTGAAAG
D--A--A--Y--Q--C--V--V--G--G--E--K--C--S--T--E--L--F--V--K--

AGCCCCCTGTGCTCATCACGCGCCCCTTGGAGGACCAGCTGGTGATGGTGGGGCAGCGGG
E--P--P--V--L--I--T--R--P--L--E--D--Q--L--V--M--V--G--Q--R--

TGGAGTTTGAGTGTGAAGTATCGGAGGAGGGGGCGCAAGTCAAATGGCTGAAGGACGGGG
V--E--F--E--C--E--V--S--E--E--G--A--Q--V--K--W--L--K--D--G--

TGGAGCTGACCCGGGAGGAGACCTTCAAATACCGGTTCAAGAAGGACGGGCAGAGACACC
V--E--L--T--R--E--E--T--F--K--Y--R--F--K--K--D--G--Q--R--H--

ACCTGATCATCAACGAGGCCATGCTGGAGGACGCGGGGCACTATGCACTGTGCACTAGCG
H--L--I--I--N--E--A--M--L--E--D--A--G--H--Y--A--L--C--T--S--

GGGGCCAGGCGCTGGCTGAGCTCATTGTGCAGGAAAAGAAGCTGGAGGTGTACCAGAGCA
G--G--Q--A--L--A--E--L--I--V--Q--E--K--K--L--E--V--Y--Q--S--

TCGCAGACCTGATGGTGGGCGCAAAGGACCAGGCGGTGTTCAAATGTGAGGTCTCAGATG
I--A--D--L--M--V--G--A--K--D--Q--A--V--F--K--C--E--V--S--D--

AGAATGTTCGGGGTGTGTGGCTGAAGAATGGGAAGGAGCTGGTGCCCGACAGCCGCATAA
E--N--V--R--G--V--W--L--K--N--G--K--E--L--V--P--D--S--R--I--

AGGTGTCCCACATCGGGCGGGTCCACAAACTGACCATTGACGACGTCACACCTGCCGACG
K--V--S--H--I--G--R--V--H--K--L--T--I--D--D--V--T--P--A--D--

AGGCTGACTACAGCTTTGTGCCCGAGGGCTTCGCCTGCAACCTGTCAGCCAAGCTCCACT
E--A--D--Y--S--F--V--P--E--G--F--A--C--N--L--S--A--K--L--H--

TCATGGAGGTCAAGATTGACTTCGTACCCAGGCAGGAACCTCCCAAGATCCACCTGGACT
F--M--E--V--K--I--D--F--V--P--R--Q--E--P--P--K--I--H--L--D--

GCCCAGGCCGCATACCAGACACCATTGTGGTTGTAGCTGGAAATAAGCTACGTCTGGACG
C--P--G--R--I--P--D--T--I--V--V--V--A--G--N--K--L--R--L--D--

TCCCTATCTCTGGGGACCCTGCTCCCACTGTGATCTGGCAGAAGGCTATCACGCAGGGGA
V--P--I--S--G--D--P--A--P--T--V--I--W--Q--K--A--I--T--Q--G--

ATAAGGCCCCAGCCAGGCCAGCCCCAGATGCCCCAGAGGACACAGGTGACAGCGATGAGT
N--K--A--P--A--R--P--A--P--D--A--P--E--D--T--G--D--S--D--E--

GGGTGTTTGACAAGAAGCTGCTGTGTGAGACCGAGGGCCGGGTCCGCGTGGAGACCACCA
W--V--F--D--K--K--L--L--C--E--T--E--G--R--V--R--V--E--T--T--

AGGACCGCAGCATCTTCACGGTCGAGGGGGCAGAGAAGGAAGATGAGGGCGTCTACACGG
K--D--R--S--I--F--T--V--E--G--A--E--K--E--D--E--G--V--Y--T--

TCACAGTGAAGAACCCTGTGGGCGAGGACCAGGTCAACCTCACAGTCAAGGTCATCGACG
```

Figure 9 (Continued)

```
          V--T--V--K--N--P--V--G--E--D--Q--V--N--L--T--V--K--V--I--D--
TGCCAGACGCACCTGCGGCCCCCAAGATCAGCAACGTGGGAGAGGACTCCTGCACAGTAC
V--P--D--A--P--A--A--P--K--I--S--N--V--G--E--D--S--C--T--V--
AGTGGGAGCCGCCTGCCTACGATGGCGGGCAGCCCATCCTGGGCTACATCCTGGAGCGCA
Q--W--E--P--P--A--Y--D--G--G--Q--P--I--L--G--Y--I--L--E--R--
AGAAGAAGAAGAGCTACCGGTGGATGCGGCTGAACTTCGACCTGATTCAGGAGCTGAGTC
K--K--K--K--S--Y--R--W--M--R--L--N--F--D--L--I--Q--E--L--S--
ATGAAGCGCGGCGCATGATCGAGGGCGTGGTGTACGAGATGCGCGTCTACGCGGTCAACG
H--E--A--R--R--M--I--E--G--V--V--Y--E--M--R--V--Y--A--V--N--
CCATCGGCATGTCCAGGCCCAGCCCTGCCTCCCAGCCCTTCATGCCTATCGGTCCCCCCA
A--I--G--M--S--R--P--S--P--A--S--Q--P--F--M--P--I--G--P--P--
GCGAACCCACCCACCTGGCAGTAGAGGACGTCTCTGACACCACGGTCTCCCTCAAGTGGC
S--E--P--T--H--L--A--V--E--D--V--S--D--T--T--V--S--L--K--W--
GGCCCCCAGAGCGCGTGGGAGCAGGAGGCCTGGATGGCTACAGCGTGGAGTACTGCCCAG
R--P--P--E--R--V--G--A--G--L--D--G--Y--S--V--E--Y--C--P--
AGGGCTGCTCAGAGTGGGTGGCTGCCCTGCAGGGGCTGACAGAGCACACATCGATACTGG
E--G--C--S--E--W--V--A--A--L--Q--G--L--T--E--H--T--S--I--L--
TGAAGGACCTGCCCACGGGGGCCCGGCTGCTTTTCCGAGTGCGGGCACACAATATGGCAG
V--K--D--L--P--T--G--A--R--L--F--R--V--R--A--H--N--M--A--
GGCCTGGAGCCCCTGTTACCACCACGGAGCCGGTGACAGTGCAGGAGATCCTGCAACGGC
G--P--G--A--P--V--T--T--E--P--V--T--V--Q--E--I--L--Q--R--
CACGGCTTCAGCTGCCCAGGCACCTGCGCCAGACCATTCAGAAGAAGGTCGGGGAGCCTG
P--R--L--Q--L--P--R--H--L--R--Q--T--I--Q--K--K--V--G--E--P--
TGAACCTTCTCATCCCTTTCCAGGGCAAGCCCCGGCCTCAGGTGACCTGGACCAAAGAGG
V--N--L--L--I--P--F--Q--G--K--P--R--P--Q--V--T--W--T--K--E--
GGCAGCCCCTGGCAGGCGAGGAGGTGAGCATCCGCAACAGCCCCACAGACACCATCCTGT
G--Q--P--L--A--G--E--E--V--S--I--R--N--S--P--T--D--T--I--L--
TCATCCGGGCCGCTCGCCGCGTGCATTCAGGCACTTACCAGGTGACGGTGCGCATTGAGA
F--I--R--A--A--R--R--V--H--S--G--T--Y--Q--V--T--V--R--I--E--
ACATGGAGGACAAGGCCACGCTGGTGCTGCAGGTTGTTGACAAGCCAAGTCCTCCCCAGG
N--M--E--D--K--A--T--L--V--L--Q--V--V--D--K--P--S--P--P--Q--
ATCTCCGGGTGACTGACGCCTGGGGTCTTAATGTGGCTCTGGAGTGGAAGCCACCCCAGG
D--L--R--V--T--D--A--W--G--L--N--V--A--L--E--W--K--P--P--Q--
ATGTCGGCAACACGGAGCTCTGGGGGTACACAGTGCAGAAAGCCGACAAGAAGACCATGG
D--V--G--N--T--E--L--W--G--Y--T--V--Q--K--A--D--K--K--T--M--
AGTGGTTCACCGTCTTGGAGCATTACCGCCGCACCCACTGCGTGGTGCCAGAGCTCATCA
E--W--F--T--V--L--E--H--Y--R--R--T--H--C--V--V--P--E--L--I--
TTGGCAATGGCTACTACTTCCGCGTCTTCAGCCAGAATATGGTTGGCTTTAGTGACAGAG
I--G--N--G--Y--Y--F--R--V--F--S--Q--N--M--V--G--F--S--D--R--
```

Figure 9 (Continued)

```
CGGCCACCACCAAGGAGCCCGTCTTTATCCCCAGACCAGGCATCACCTATGAGCCACCCA
 A--A--T--T--K--E--P--V--F--I--P--R--P--G--I--T--Y--E--P--P--

ACTATAAGGCCCTGGACTTCTCCGAGGCCCCAAGCTTCACCCAGCCCCTGGTGAACCGCT
 N--Y--K--A--L--D--F--S--E--A--P--S--F--T--Q--P--L--V--N--R--

CGGTCATCGCGGGCTACACTGCTATGCTCTGCTGTGCTGTCCGGGGTAGCCCCAAGCCCA
 S--V--I--A--G--Y--T--A--M--L--C--C--A--V--R--G--S--P--K--P--

AGATTTCCTGGTTCAAGAATGGCCTGGACCTGGGAGAAGACGCCCGCTTCCGCATGTTCA
 K--I--S--W--F--K--N--G--L--D--L--G--E--D--A--R--F--R--M--F--

GCAAGCAGGGAGTGTTGACTCTGGAGATTAGAAAGCCCTGCCCCTTTGACGGGGGCATCT
 S--K--Q--G--V--L--T--L--E--I--R--K--P--C--P--F--D--G--G--I--

ATGTCTGCAGGGCCACCAACTTACAGGGCGAGGCACGGTGTGAGTGCCGCCTGGAGGTGC
 Y--V--C--R--A--T--N--L--Q--G--E--A--R--C--E--C--R--L--E--V--

GAGTGCCTCAGTGACCAGGCTGGCTCCTGGGGATGGCCAGGTACAACCGGATGCCAGCCC
 R--V--P--Q--*.............................................
```

IDENTIFYING SUSCEPTIBILITY TO CARDIAC HYPERTROPHY

CROSS-REFERENCE TO RELATED APPLICATIONS

This application claims the benefit of U.S. Provisional Application Ser. No. 60/732,776, filed Nov. 1, 2005.

BACKGROUND

1. Technical Field

This document provides methods and materials related to identifying, assessing, and predicting hypertrophic cardiomyopathy (HCM) in mammals. For example, this document provides methods and materials for using mutations (e.g., mutations in ZASP and MYBPC3 nucleic acids) to identify, assess, and predict HCM in mammals (e.g., humans).

2. Background Information

Once thought to be a rare disease, HCM is now understood as a relatively common, potentially heritable disorder affecting about 1 in 500 people. Although the overall annual incidence of sudden death is around one percent, HCM represents the most common identifiable cause of sudden death in young people. HCM is characterized morphologically by thickening of the left ventricular wall, fibrosis, and myocyte disarray in the absence of extenuating extrinsic factors such as hypertension and aortic valve disease. The clinical presentation is underscored by pronounced phenotypic heterogeneity ranging from an asymptomatic course to sudden cardiac death during childhood.

SUMMARY

This document provides methods and materials related to identifying, assessing, and predicting HCM in mammals. For example, this document provides methods and materials for using mutations (e.g., mutations in ZASP and MYBPC3 nucleic acids) to identify, assess, and predict HCM in mammals (e.g., humans). Determining whether or not mammals such as humans have one or more of the mutations provided herein can allow clinicians to determine whether or not the mammal has HCM, is susceptible to develop HCM, is likely to develop HCM at an early age, or is likely to develop severe HCM. For example, the presence of multiple mutations associated with HCM can indicate that a human is susceptible to develop severe HCM. Such information can be used to guide therapeutic or preventive methods. As described herein, mammals having mutations associated with HCM can be identified by obtaining samples (e.g., blood samples) from the mammals and analyzing the samples using, for example, polymerase chain reaction, denaturing high-performance liquid chromatography, and DNA sequencing.

In general, one aspect of this document features a method for determining a human's susceptibility to develop hypertrophic cardiomyopathy. The method comprises, or consists essentially of, determining whether or not a human comprises genomic nucleic acid comprising one or more mutations listed in Table 1, where the presence of the one or more mutations indicates that the human is susceptible to develop hypertrophic cardiomyopathy. The determining step can comprise analyzing DNA, analyzing RNA, analyzing a polypeptide sample, or analyzing a blood sample from the human.

In another embodiment, this document features a method for determining whether or not a human comprises one or more mutations listed in Table 1. The method comprises, or consists essentially of, analyzing a sample from the human using polymerase chain reaction, denaturing high-performance liquid chromatography, or sequencing. The sample can be blood or genomic DNA.

In another embodiment, this document features a substantially pure amplification product comprising, or consisting essentially of, a nucleic acid molecule less than 2500 nucleotides in length, where the nucleic acid molecule comprises one or more mutations listed in Table 1.

In yet another embodiment, this document features an isolated polynucleotide having the ability to hybridize to a nucleic acid molecule comprising a mutation listed in Table 1 under hybridization conditions and not having the ability to hybridize to a second nucleic acid molecule not comprising said mutation under the same hybridization conditions. The polynucleotide, when used in an amplification reaction with a primer, can amplify the nucleic acid molecule and not the second nucleic acid molecule. The polynucleotide can be fluorescently or radioactively labeled.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 8 is a listing of amino acid sequences of ZASP polypeptides (SEQ ID NO:2 and SEQ ID NO:4) and nucleic acid sequences encoding ZASP polypeptides (SEQ ID NO:1 and SEQ ID NO:3).

FIG. 9 is a listing of an amino acid sequence of a MYBPC3 polypeptide (SEQ ID NO:6) and a nucleic acid sequence encoding a MYBPC3 polypeptide (SEQ ID NO:5).

DETAILED DESCRIPTION

Figure 1:
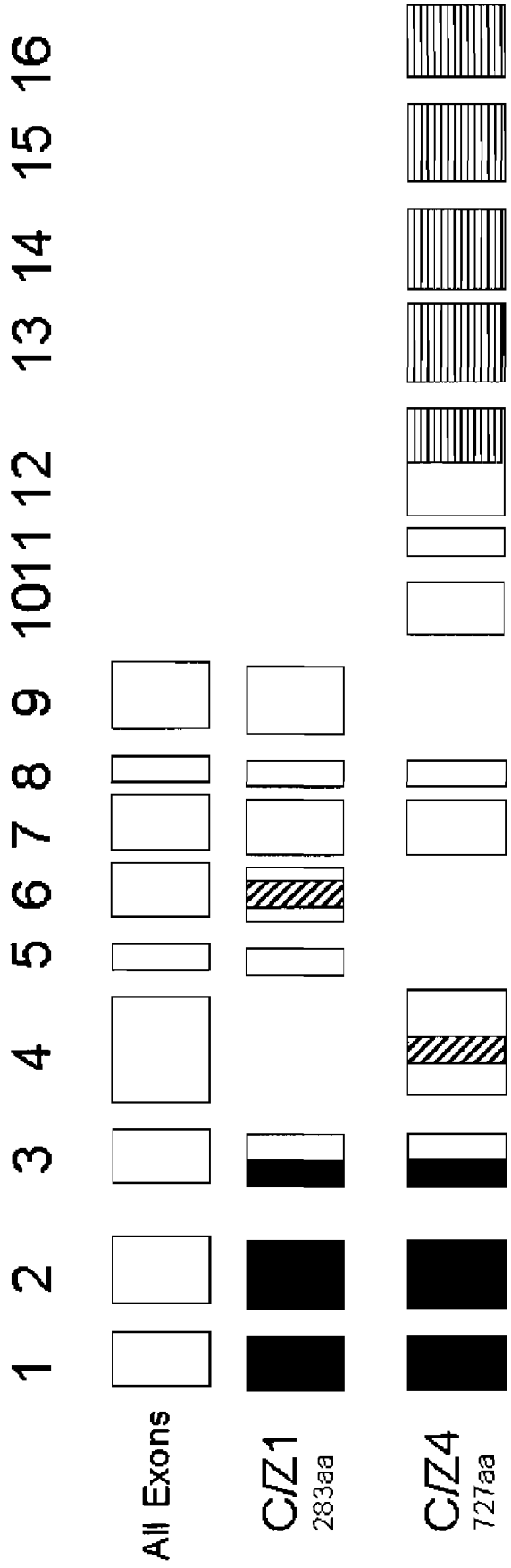
FIG. 1 is a schematic diagram of the genomic structure of Z-band alternatively spliced PDZ-containing protein (ZASP). The intron-exon organization of ZASP is depicted in the top row. The middle and bottom rows depict the genomic structures of two alternatively spliced isoforms of ZASP found in heart. Solid black rectangles represent exons encoding PDZ domains. Diagonal rectangles represent ZM-motifs. Rectangles with horizontal lines represent LIM domains.

This document provides methods and materials related to detecting one or more mutations in ZASP and MYBPC3 nucleic acids. For example, this document provides methods for determining whether or not a mammal contains ZASP or MYBPC3 nucleic acid having a mutation linked to hypertrophic cardiomyopathy (HCM). The mammal can be any type of mammal including, without limitation, a mouse, rat, dog, cat, horse, sheep, goat, cow, pig, monkey, or human. The term "ZASP nucleic acid" as used herein refers to any nucleic acid that encodes a ZASP polypeptide or any fragment of such a nucleic acid. Examples of ZASP nucleic acid include, without limitation, the nucleic acid sequences set forth in FIG. 8 (SEQ ID NO:1 and SEQ ID NO:3) and the nucleic acid sequence set forth in GenBank® Accession Number NM_007078. The term "MYBPC3 nucleic acid" as used herein refers to any nucleic acid that encodes a MYBPC3 polypeptide or any fragment of such a nucleic acid. Examples of MYBPC3 nucleic acid include, without limitation, the nucleic acid sequence set forth in FIG. 9 (SEQ ID NO:5) and the nucleic acid sequence set forth in GenBank® Accession Number NM_000256.

The methods and materials provided herein can be used to determine whether or not ZASP or MYBPC3 nucleic acid of a mammal (e.g., human) contains a mutation or combination of mutations. Mutations in ZASP or MYBPC3 nucleic acid can include point mutations, insertions, and deletions (e.g., those mutations identified herein as being associated with HCM disease). In some embodiments, the methods and materials provided herein can be used to determine whether both alleles of ZASP or MYBPC3 of a mammal contain mutations (e.g., either the same mutation(s) on both alleles, or separate mutations on each allele), or whether only a single ZASP or MYBPC3 allele of the mammal contains a mutation. The identification of one or more mutations on an allele can be used to diagnose HCM in a mammal, typically when known clinical symptoms of HCM also are present. The identification of other mutations (e.g., sequence mutations not known to be associated with HCM) can be used to support a potential diagnosis of HCM. The identification of a mutation on only one ZASP or MYBPC3 allele can serve as an indicator that the mammal is a carrier.

Any suitable method can be used to detect a mutation within ZASP or MYBPC3 nucleic acid. For example, mutations can be detected by sequencing exons, introns, or untranslated sequences, denaturing high performance liquid chromatography (DHPLC; Underhill et al., *Genome Res.*, 7:996-1005 (1997)), allele-specific hybridization (Stoneking et al., *Am. J Hum. Genet.*, 48:370-382 (1991); and Prince et al., *Genome Res.*, 11(1):152-162 (2001)), allele-specific restriction digests, mutation specific polymerase chain reactions, restriction fragment length polymorphism detection, single-stranded conformational polymorphism detection (Schafer et al., *Nat. Biotechnol.* 15:33-39 (1998)), infrared matrix-assisted laser desorption/ionization mass spectrometry (WO 99/57318), and combinations of such methods.

In some embodiments, genomic DNA can be used to detect one or more mutations within ZASP or MYBPC3 nucleic acid. Genomic DNA typically is extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. In some cases, genomic DNA can be extracted with kits such as the QIAamp® Tissue Kit (Qiagen, Chatsworth, Calif.), the Wizard® Genomic DNA purification kit (Promega, Madison, Wis.), the Puregene DNA Isolation System (Gentra Systems, Inc., Minneapolis, Minn.), and the A.S.A.P.3 Genomic DNA isolation kit (Boehringer Mannheim, Indianapolis, Ind.).

In some embodiments, RNA can be used to detect one or more mutations within ZASP or MYBPC3 nucleic acid. RNA is typically extracted from a biological sample (e.g., peripheral blood or mucosal scrapings). Methods for extracting RNA are known in the art and include phenol-chloroform and TRIzol® Reagent extraction and the use of kits such as RNeasy® (Qiagen), RNAgents® Total RNA Isolation System (Promega), and VERSAGENE™ RNA Purification Kit (Gentra).

An amplification step can be performed before proceeding with the detection method. For example, exons or introns of the ZASP or MYBPC3 nucleic acid can be amplified and then directly sequenced. In some cases, cDNA can be produced from RNA prior to amplification. Dye primer sequencing can be used to increase the accuracy of detecting heterozygous samples.

Mutations within ZASP and MYBPC3 nucleic acid can be detected by, for example, DHPLC analysis of ZASP and MYBPC3 nucleic acid, respectively. Genomic DNA can be isolated from a mammal (e.g., a human), and sequences from one or more regions of a ZASP or MYBPC3 nucleic acid can be amplified (e.g., by PCR) using pairs of oligonucleotide primers. The primer pairs listed in Tables 3 and 5, for example, can be used to amplify all 16 coding exons of human ZASP and all 34 coding exons of human MYBPC3 nucleic acid, respectively. After amplification, PCR products can be denatured and reannealed, such that an allele containing a mutation can reanneal with a wild-type allele to form a heteroduplex (i.e., a double-stranded nucleic acid with a mismatch at one or more positions). The reannealed products then can be subjected to DHPLC, which detects heteroduplexes based on their altered melting temperatures, as compared to homoduplexes that do not contain mismatches. Samples containing heteroduplexes can be sequenced by standard methods to specifically identify the mutant nucleotides. Examples of specific mutations are provided in Table 1.

TABLE 1

Mutations associated with HCM

| Mutation | Nucleotide Change | Nucleic Acid |
|---|---|---|
| V125M | ctg > atg | ZASP |
| I158V | ccc > gtc | ZASP |
| D366N | gac > aac | ZASP |
| Y468S | tat > tct | ZASP |
| Q519P | ag > ccg | ZASP |
| V601I | tt > att | ZASP |
| P615L | cg > ctg | ZASP |
| A184V | cc > gtc | ZASP |
| P419N | ct > cgt | ZASP |
| G5R | ggg > cgg | MYBPC3 |
| splice | a > g int − 2 | MYBPC3 |
| T59 fs/49 | del gggcacacggc (SEQ ID NO: 103) | MYBPC3 |
| V219L | gtc > ctc | MYBPC3 |
| V256I | gtc > atc | MYBPC3 |
| D389 fs/15 | del c | MYBPC3 |
| I411 fs/0 | del tt | MYBPC3 |
| R458H | cgc > cag | MYBPC3 |
| G490R | ggg > agg | MYBPC3 |
| E546 fs/19 | del gt | MYBPC3 |
| C566 fs/3 | del ga | MYBPC3 |
| D604V | gac > gtc | MYBPC3 |
| D605N | gac > aac | MYBPC3 |
| P609L | cct > ctt | MYBPC3 |
| R733C | cgc > tgc | MYBPC3 |
| D770N | gac > aac | MYBPC3 |
| splice | a > g int − 2 | MYBPC3 |
| W792R | tgg > cgg | MYBPC3 |
| P794 fs/26 | del g | MYBPC3 |
| K811del | del aag | MYBPC3 |
| W818 fs/11 | del atgcg | MYBPC3 |
| S830 fs/1 | ins t | MYBPC3 |
| E843X | gag > tag | MYBPC3 |
| Y847X | tac > tag | MYBPC3 |
| A851 fs/26 | del c | MYBPC3 |
| A851 fs/31 | ins t, ggc > tgc | MYBPC3 |
| I852 fs/25 | del g | MYBPC3 |
| W890X | tgg > tga | MYBPC3 |
| R943X | cga > tga | MYBPC3 |
| Q998E | cag > gag | MYBPC3 |
| Q998R | cag > cgg | MYBPC3 |
| G1041 fs/5 | Ins aa | MYBPC3 |
| F1113I | ttc > atc | MYBPC3 |
| C1124X | tgc > atc | MYBPC3 |
| I1131T | att > act | MYBPC3 |

Allele specific hybridization also can be used to detect mutations in ZASP or MYBPC3 nucleic acid, including complete haplotypes of a mammal. For example, samples of DNA or RNA from one or more mammals can be amplified using pairs of primers, and the resulting amplification products can be immobilized on a substrate (e.g., in discrete regions). Hybridization conditions can be selected such that a nucleic acid probe specifically binds to the sequence of interest, e.g., a ZASP or MYBPC3 nucleic acid containing a particular mutation. Such hybridizations can be performed under high stringency, as some nucleotide mutations include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS)) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently or radioactively) to facilitate detection. In some embodiments, one of the primers used in the amplification reaction can be biotinylated (e.g., 5' end of reverse primer), and the resulting biotinylated amplification product can be immobilized on an avidin or streptavidin coated substrate.

Allele-specific restriction digests can be performed to detect mutations in ZASP or MYBPC nucleic acid. For example, sequences from one or more regions of a ZASP or MYBPC3 nucleic acid can be amplified (e.g., by PCR) using pairs of oligonucleotide primers. The amplification products can then be digested with a restriction enzyme to detect mutations that introduce or remove a restriction site in a ZASP or MYBPC3 nucleic acid.

Real-time PCR can be used to detect mutations in ZASP or MYBPC3 nucleic acid. For example, genomic DNA or cDNA can be amplified using pairs of oligonucleotide primers (e.g., the primer pairs listed in Tables 3 and 5) in the presence of one or more nucleic acid probes or a dye that fluoresces when bound to double stranded DNA (e.g., SYBR® Green). The nucleic acid probes can be labeled (e.g., fluorescently) such that the label is detectable when hybridized to the sequence of interest (e.g., a ZASP or MYBPC3 nucleic acid). After amplification, the reaction can be subjected to a melting curve analysis. Melting curve analysis can include slowly increasing the temperature of the real-time PCR product and measuring fluorescence to determine the temperature at which the probe or dye dissociates from the amplification product (i.e., the melting temperature). If a probe is used, the melting temperature can indicate whether the sequence of interest is an exact match to the probe, or if a mismatch (e.g., a mutation) is present in the sequence of interest. If a fluorescent dye is used, the detection of more than one melting temperature can indicate the presence of at least one mutation in the sequence of interest.

In some cases, polypeptide analysis can be used to detect mutations in ZASP or MYBPC3 nucleic acid. For example, an antibody that specifically binds to a polypeptide encoded by a nucleic acid containing a mutation can be used in ELISA assays or immunoblot assays to detect the presence of such a mutation.

Other methods also can be used to detect mutations. For example, conventional and field-inversion electrophoresis can be used visualize basepair changes. In addition, Southern blotting and hybridization can be used to detect larger rearrangements such as deletions and insertions.

A mammal containing a mutation in ZASP or MYBPC3 nucleic acid or both can be classified as having an elevated risk of developing HCM. An "elevated risk" is a risk greater than that of a comparable mammal who contains wild-type ZASP and MYBPC3 nucleic acid at both alleles. A human classified as having an elevated risk of developing HCM can have one or more of the mutations listed in Table 1.

A mammal containing more than one mutation (e.g., two, three, four, five, or more mutations) in ZASP or MYBPC3 nucleic acid or both can be classified as having an elevated risk of developing a severe form of HCM compared to a mammal containing wild-type ZASP and MYBPC3 nucleic acid at both alleles. Compared to non-severe HCM, a severe form of HCM can be characterized by a younger age at onset of the disease, a greater degree of hypertrophy, and a higher surgical intervention rate. A human classified as having an elevated risk of developing severe HCM can have more than one of the mutations listed in Table 1.

A mammal containing a mutation in ZASP nucleic acid and a sarcomeric mutation (e.g., a mutation in MYBPC3, MYH7, MYL2, MYL3, TNNT2, TNNI3, TPM1 or ACTC nucleic acid) can be classified as having an elevated risk of developing HCM at a younger age than a mammal containing a mutation in ZASP nucleic acid and not containing a sarcomeric mutation. For example, a mammal having a ZASP mutation and a sarcomeric mutation can be diagnosed with HCM at an age of about 34 years (e.g., about 26, 27, 28, 29, 30, 31, 32, 33, 35, 36, 37, 38, 39, or 40 years), whereas a mammal having a ZASP mutation and lacking a sarcomeric mutation can be diagnosed with HCM at an age of about 51 years (e.g., about 43, 44, 45, 47, 49, 53, 55, 57, 62, 65, or 70 years). A ZASP mutation can include, without limitation, V125M, I158V, D366N, Y468S, Q519P, V601I, P615L, A184V, D117N, S196L, or P419N. Sarcomeric mutations can include previously identified mutations, such as those described elsewhere (Van Driest et al., *J. Am. Coll. Cardiol.*, 44:602-10 (2004)).

This document also provides kits that can be used to determine whether or not mammals contain mutations described herein. Such kits can contain reagents for performing a genetic analysis, containers for reagents or samples (e.g., blood samples), and packaging materials. Reagents can include, without limitation, reagents for performing FISH, CGH, or any other technique described herein. A container can be labeled for use for the diagnosis and/or prognosis of a human relating to the development and treatment of HCM. The kit can contain separate containers, dividers, or compartments for the reagents and packaging material.

Packaging material can be descriptive, instructional, marketing or other material that relates to the methods described herein and/or the use of the reagents for the methods described herein. For example, the packaging material can describe methods for performing a genetic analysis on a human and subsequently diagnosing the human as being at risk (or not) for HCM, and/or delivering a prognosis of the human relating to survival time, likelihood of responding to therapy, etc. In addition, or in an alternative, packaging material can include contact information, e.g., a physical address, email address, website, or telephone number, where a user of the kit can obtain substantive information about performing a genetic analysis and interpreting the results, particularly as they apply to a human's likelihood of developing HCM and a subsequent prognosis.

Packaging material can be in any form. In many cases, packaging material, e.g., instructions, can be provided in printed form, e.g., a printed text, drawing, and/or photograph, e.g., a label or printed sheet.

This document also provides isolated nucleic acids that can include a fragment of at least about 15 nucleotides (e.g., at least about 16, 17, 20, 22, 25, 30, 35, 40, 50, 75, 100, 150, 300, 500, or more nucleotides) from a ZASP or MYBPC3 nucleic acid. The ZASP or MYBPC3 nucleic acid can contain one or more (e.g., two, three, four, five, six, seven, eight, nine, ten, or more) of the mutations provided herein. For example, an isolated nucleic acid can contain 100 nucleotides from human ZASP or MYBPC3 nucleic acid with two of the mutations set forth in Table 1.

This document also provides amplification products comprising nucleic acid molecules containing, for example, one or more mutations listed in Table 1. Such products can be amplified from any nucleic acid-containing sample from a mammal, such as a blood sample. The nucleic acid can be any nucleic acid, such as genomic DNA, cDNA, or RNA. In addition, the nucleic acid can be purified from the sample prior to amplification. Any suitable method can be used to obtain the amplification products. For example, amplification products containing one or more mutations listed in Table 1 can be obtained by performing PCR or RT-PCR using, e.g., primers listed in Tables 3 and 5. The amplification product can be less than about 2500 nucleotides in length (e.g., less than 2100, 2000, 1800, 1500, 1200, 1000, 800, 750, 690, 500, 420, 300, 280, 240, 200, 150, 125, 100, 70, or 50 nucleotides in length). An amplification product can be purified by any method, such as by using a Qiagen (Valencia, Calif.) kit for purification of PCR products. In some cases, an amplification product provided herein can be a substantially pure amplification product. For example, an amplification product can contain a particular nucleic acid molecule that is greater than about 50 percent pure (e.g., greater than 55, 60, 64, 70, 75, 78, 80, 83, 87, 90, 92, 93, 95, 96, 97, 98, or 99 percent pure). A substantially pure amplification product is typically visible as a single band on an agarose gel.

The terms "polynucleotide" and "nucleic acid" are used interchangeably herein. The term "isolated nucleic acid," as used herein, refers to a nucleic acid that is separated from other nucleic acid molecules that are present in a mammalian genome, including nucleic acids that normally flank one or both sides of the nucleic acid in a mammalian genome (e.g., nucleic acids that encode non-ZASP and non-MYBPC3 polypeptides). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Typically, the isolated nucleic acids provided herein are at least about 8 nucleotides in length. For example, a nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, 1000, 1500, or 2000 nucleotides in length). The isolated nucleic acids provided herein can be in a sense or antisense orientation, can be complementary to a ZASP or MYBPC3 nucleic acid (e.g., SEQ ID NO:1, SEQ ID NO:3, and SEQ ID NO:5), and can be DNA, RNA, or nucleic acid analogs. Nucleic acid analogs can be modified at the base moiety, sugar moiety, or phosphate backbone to improve, for example, stability, hybridization, or solubility of the nucleic acid.

This document also provides isolated polynucleotides having the ability to hybridize to nucleic acid containing one or more particular mutations listed in Table 1, while not having the ability to hybridize to nucleic acid lacking those particular one or more mutations listed in Table I under the same hybridization conditions. Such isolated polynucleotides can function as primers that can be used in PCR reactions to amplify nucleic acids containing one or more mutations described herein without amplifying the corresponding nucleic acid lacking such one or more mutations. In some cases, isolated polynucleotides can also be labeled (e.g., fluorescently or radioactively) and used as probes to detect nucleic acids containing one or more mutations listed in Table 1 without detecting nucleic acids that lack such mutations.

As used herein, "mutant" refers to any alteration in a reference ZASP or MYBPC3 sequence, and includes mutations that occur in coding and non-coding regions, including exons, introns, and untranslated sequences. Nucleotides are referred to herein by the standard one-letter designation (A, C, G, or T). Mutations include single nucleotide substitutions, deletions of one or more nucleotides, and insertions of one or more nucleotides. The reference ZASP nucleic acid sequence can be the sequence set forth in FIG. 8, SEQ ID NO:1, SEQ ID NO:3, or in GenBank® (Accession Number NM_007078). The reference ZASP amino acid sequence can be the sequences set forth in FIG. 8, SEQ ID NO:2, or SEQ ID NO:4. The reference MYBPC3 nucleic acid sequence can be the sequence set forth in FIG. 9, SEQ ID NO:5, or in GenBank® (Accession Number NM_000256). The reference MYBPC3 amino acid sequence can be the sequence set forth in FIG. 9 or SEQ ID NO:6.

Isolated nucleic acids can be produced by standard techniques, including, without limitation, common molecular cloning and chemical nucleic acid synthesis techniques. For example, polymerase chain reaction techniques can be used to obtain an isolated nucleic acid containing a fragment of ZASP or MYBPC3 nucleic acid with a mutation.

The invention will be further described in the following examples, which do not limit the scope of the invention described in the claims.

EXAMPLES

Example 1

Identifying ZASP Mutations in HCM Patients

Mutational analyses were performed on a cohort of 389 unrelated patients with HCM. As presented in Table 2, 215 of the HCM patients were male, with a maximum left ventricular wall thickness (LVWT) of 22±6 mm. The mean age at diagnosis was 41±19 years. Two hundred and sixteen patients (55%) had cardiac symptoms at presentation, and 60 (15%) had a cardioverter-defibrillator implanted. The mean LVWT was 21.6±6 mm. Of the 389 HCM patients, 161 (41%) were treated in part by a surgical myectomy, reflecting the surgical referral bias and subsequent over-representation of obstructive HCM in this cohort. Approximately one-third (31%) had a family history of HCM, whereas one-seventh (14%) was found to have a family history of unexplained death. An HCM-associated sarcomeric mutation was previously demonstrated in 147 of the 389 subjects (38%), with the majority of the genotype positive patients having mutations involving either MYBPC3 or MYH7 (Table 2). A total of 13 unrelated patients harbored only mutations involving the constituents of the cardiac thin filament: troponin T, troponin I, tropomyosin, and actin.

TABLE 2

Demographics of an HCM cohort

| Unrelated Patients with HCM | N = 389 |
|---|---|
| Male/female | 215/174 |
| Age at diagnosis | 41.2 ± 19 |
| Mean LVWT (mm) | 21.6 ± 6 |
| Mean peak LVOT gradient (mmHG) | 46.6 ± 42 |
| No. presenting with cardiac symptoms | 55.5% |
| Positive family history of HCM | 31% |
| Positive family history of SCD | 14% |
| Surgical myectomy | 161 (41%) |
| Pacemaker | 67 (17%) |
| ICD | 60 (15%) |
| Number of patients with previously reported sarcomeric mutations | 147 (38%) |
| MYBPC | 63 (16.2%) |
| MYH7 | 54 (13.8%) |
| MYL2 | 7 (1.8%) |
| TNNT2 | 6 (1.5%) |
| TNNI3 | 4 (1.0%) |
| TPMI | 2 (0.5%) |
| ACTC | 1 (0.3%) |
| Number of patients with mutations involving ZASP | 20 (5.1%) |

HCM = hypertrophic cardiomyopathy;
LVOT = left ventricular outflow tract;
LVWT = left ventricular wall thickness;
SCD = sudden cardiac death;
ICD = implantable cardioverter-defibrillator Following written informed consent for the IRB-approved research protocol, DNA was extracted from blood samples using Purgene DNA extraction kits (Gentra, Inc., Minneapolis, Minn,). Results from comprehensive open reading frame/splice site mutational analysis of eight nucleic acids encoding sarcomeric polypeptides (MYBPC3, MYH7, MYL2, MYL3, TNNT2, TNNI3, TPM1 and ACTC) were reported previously (Van Driest et al., *Circulation* 108:445-451 (2003); Van Driest et al., *J Am Coll Cardiol.* 44:1903-1910 (2004); Van Driest et al., *J Am Coll Cardiol.* 44:602-10 (2004)).

All 16 polypeptide-encoding exons of ZASP, along with flanking intronic regions, were amplified by polymerase chain reaction (PCR) using previously designed primers (Vatta et al., *J Am Coll Cardiol.* 42:2014-27 (2003); Table 3). Exon 4 was divided into two overlapping regions of interest for optimal mutational analysis. Each amplicon was assessed for heterozygosity by denaturing high performance liquid chromatography (DHPLC) performed using the Transgenomic system (Omaha, Nebr.). Each sample with an abnormal elution profile was sequenced using an ABI Prism 377 instrument (Applied Biosystems, Foster City, Calif.) to characterize the difference between the wild-type and varient alleles (Ackerman et al., *Pediatr Res.* 44:148-153 (1998)).

TABLE 3

ZASP primers

| Exon | Forward Primer | Reverse Primer |
|---|---|---|
| 1 | GTGCCCTCTCACTCAACCCT (SEQ ID NO:7) | ACACATGCCCTCCTCCAAGC (SEQ ID NO:8) |
| 2 | TGGCCTTTCCTCAGGACCAC (SEQ ID NO:9) | TCCTGCACAGTTTTGTAGCC (SEQ ID NO:10) |

TABLE 3-continued

ZASP primers

| Exon | Forward Primer | Reverse Primer |
|---|---|---|
| 3 | TGACTCTGGCTCTCTCTTGCT (SEQ ID NO:11) | TCCAGGAACCAGGGCTGAGT (SEQ ID NO:12) |
| 4 | GGCTCGCGCTAACACATCTG (SEQ ID NO:13) | GCCACCTGTGGAGAGCTGTA (SEQ ID NO:14) |
| 5 | CACTCCTTGCTCTCCTCACC (SEQ ID NO:15) | CTCTATCCACGCCAGACACA (SEQ ID NO:16) |
| 6 | TGTAACCGCCACCTGTTGCC (SEQ ID NO:17) | TCCAGGAGGTCCAACGTGAG (SEQ ID NO:18) |
| 7 | CCACCAATGGGCATGGAGCA (SEQ ID NO:19) | AGCAGGACTCCCTGGCTTCT (SEQ ID NO:20) |
| 8 | TTGCTGTGTCTCCCGTGAGT (SEQ ID NO:21) | GAGGTCCCTTCCATGAGTGA (SEQ ID NO:22) |
| 9 | GGTGAACACATTCCCTAACC (SEQ ID NO:23) | CCCAGCAGAGTTATACATTG (SEQ ID NO:24) |
| 10 | GCTCCCTTGACCTGTTGTCT (SEQ ID NO:25) | GCCCTAACTACCTTGGACAC (SEQ ID NO:26) |
| 11 | GGCTGTCCTTCTGGGTGTAA (SEQ ID NO:27) | TCTTGGCTCTTGTGGCTCCT (SEQ ID NO:28) |
| 12A | CATTTCTCTGGCTAGGAGTG (SEQ ID NO:29) | CTGGGAGAAGCTATCATCTG (SEQ ID NO:30) |
| 12B | TGCACCCTCGGTGGCCTACA (SEQ ID NO:31) | CTCCCAACCAGGGCTCAGAC (SEQ ID NO:32) |
| 13 | GTTCTGGGAGCTGCCTTACT (SED ID NO:33) | GGAAGAGACATGGGTCAGAG (SEQ ID NO:34) |
| 14 | AGTCAAGCCCGCTCCCTCTC (SEQ ID NO:35) | CACATGCCATCGAAGTGTTC (SEQ ID NO:36) |
| 15 | TGATTTGGGGTTTGTCTTGG (SEQ ID NO:37) | CTAGCGTGGCAAGGTATGTA (SEQ ID NO:38) |
| 16 | GTCTCACGCAGGTCTGTTCT (SEQ ID NO:39) | GCTTCCTCTCTCTCCCCATT (SEQ ID NO:40) |

To verify with 95% confidence that the true allelic frequency of identified varients was less than 0.5%, DNA samples derived from 100 healthy African Americans and 200 healthy Caucasian Americans were screened for exons containing non-synonymous mutations (600 alleles; Coriell Laboratories, Camden, N.J.). This was based on exact binomial confidence intervals for an allele frequency, allowing exclusion of each variant from being a common polymorphism when absent in 600 reference alleles. In the case of particular mutations, additional control DNA samples were provided either by another study (Vatta et al., *J Am Coll Cardiol.* 42:2014-27 (2003)) or by a cohort of unrelated patients referred for long QT syndrome genetic testing who did not meet electrocardiographic voltage-criteria for cardiac hypertrophy.

The non-synonymous mutations were annotated using the single letter convention. For example, D117N indicates that the wild type aspartic acid (D) at residue 117 was replaced by asparagine (N). The amino acid position was designated according to a previously established numbering system (Vatta et al., *J Am Coll Cardiol.* 42:2014-27 (2003)), which varied for the two different cardiac isoforms of ZASP (FIG. 1). Exons 5, 6, and 9 were numbered based on the 283 amino acid isoform, C/Z1 (SEQ ID NO:2), which contains exons 1-3 and 5-9. The remaining exons were numbered based on the 727 amino acid isoform, C/Z4 (SEQ ID NO:4), which contains exons 1-4, 7-8, and 10-16.

Each variant was analyzed to determine the nature of the amino acid substitution. Localization of each variant within known domains was also analyzed. In addition, the conservation of each variant was identified through homologous alignment with multiple species, and predicted effects on secondary structure were examined using the PredictProtein server (Rost et al., *Nucleic Acids Res.* 32:W321-6 (2004)).

Differences between continuous variables were assessed using analysis of variance (ANOVA). Pairwise differences were then determined using Fisher Protected Least Significant Difference post-hoc testing. Binomial confidence intervals excluded each variant from being a common polymorphism. Nominal variables were analyzed by contingency tables or z-tests. A probability value of less than 0.05 was considered significant.

Comprehensive mutational analyses of the 16 exons of ZASP indicated that 20 out of 389 unrelated patients (5.1%) possessed a putative HCM-associated mutation. Clinical phenotypes associated with the 20 patients who were genotype positive for perturbations in ZASP are summarized in Table 4. This subset was comprised of seven males and thirteen females diagnosed with HCM at an average age of 45.6±18 years, with a LVWT of 18±3 mm. The majority of patients were of Caucasian ethnicity (19/20). The average New York Heart Association (NYHA) classification was 2±1.1 (nine class I patients, four class II patients, five class III patients, and two class IV patients). Six patients (30%) had had a surgical myectomy. None of the 20 ZASP-positive patients with HCM displayed any overt manifestation of either proximal or distal skeletal muscle weakness. With respect to prior mutation scanning of eight sarcomeric nucleic acids in this cohort, six of the 20 ZASP genotype positive patients hosted additional sarcomeric mutations, including three with a frameshift mutation in MYBPC3 (cases 15, 16, and 17), one with a MYBPC3 missense mutation (case 19), and two with mutations in MYH7 (cases 18 and 20).

TABLE 4

Clinical profiles of HCM patients with a ZASP mutation

| Case | ZASP Mutation (exon) | Additional Sarcomeric mutation | Age (y)/ Sex | Race‡ | Age at Dx | Symptoms at Presentation | Subsequent symptoms |
|---|---|---|---|---|---|---|---|
| 1 | D117N (6) | — | 47/M | 1 | 29 | Angina, dyspnea | Angina, dyspnea |
| 2 | V125M (4A) | — | 67/F | 1 | 61 | Asymptomatic | (Pre)syneope |
| 3 | V125M (4A) | — | 79/M | 1 | 73 | Asymptomatic | Deceased |
| 4 | V125M (4A) | — | 85/M | 1 | 58 | Angina | Angina, dyspnea |

TABLE 4-continued

Clinical profiles of HCM patients with a ZASP mutation

| | | | | | | | |
|---|---|---|---|---|---|---|---|
| 5 | V125M (4A) | — | 64/F | 1 | 60 | Asymptomatic | Dyspnea |
| 6 | I158V (6) | — | 75/F | 1 | 65 | Angina | Angina, dyspnea |
| 7 | I158V (6) | — | 47/F | 1 | 40 | Angina, dyspnea, presyncope | Angina, dyspnea, presyncope |
| 8 | S196L (4B) | — | 76/F | 1 | 73 | Dyspnea, angina | Dyspnea, angina |
| 9 | S196L (4B) | — | 69/F | 1 | 63 | Asymptomatic | Angina, dyspnea, presyncope |
| 10 | D366N (10) | — | 80/M | 1 | 68 | Angina, dyspnea, presyncope | Angina, dyspnea, presyncope |
| 11 | Y468S (12A) | | 53/M | 2 | 46 | Angina, dyspnea | Angina, dyspnea |
| 12 | Q519P (12B) | — | 28/F | 1 | 21 | Angina, dyspnea, syncope | Angina, dyspnea, syncope |
| 13 | V601I (13) | — | 40/M | 1 | 24 | Asymptomatic | Asymptomatic |
| 14 | P615L (13) | — | 36/M | 1 | 28 | Dyspnea, syncope | Dyspnea, syneope |
| 15 | D117N (6) | Q791 fs/40 MYBPC3 | 46/M | 1 | 32 | Asymptomatic | Dyspnea |
| 16 | V125M(4A) | A954 fs/94 MYBPC3 | 44/M | 1 | 36 | Dyspnea | Angina, dyspnea |
| 17 | A184V (4B) | A851 fs/26 MYBPC3 | 34/M | 1 | 30 | Syncope | Syncope |
| 18 | P419N (12A) | D778V MYH7 | 60/M | 1 | 43 | Asymptomatic | Asymptomatic |
| 19 | Q519P (12B) | V219L MYBPC3 | 48/F | 1 | 41 | Angina, dyspnea, presyncope | Angina, dyspnea, presyncope |
| 20 | Q519P (12B) | A797T MYH7 | 28/F | 1 | 20 | Angina, dyspnea, presyncope | Angina, dyspnea, presyncope |

| Case | AF | Max. LVWT (mm) | Resting LVOTO (mm Hg) | FH of HCM | FH of SCD (Age at SCD) | Treatment |
|---|---|---|---|---|---|---|
| 1 | No | 23 | 75 | Yes* | No | — |
| 2 | No | 16 | 5 | No | No | — |
| 3 | No | n/a | n/a | No | No | — |
| 4 | Yes | 22 | 44 | No | No | Septal ablation |
| 5 | No | 17 | 40 | No | No | — |
| 6 | No | 19 | 0 | Yes* | No | — |
| 7 | No | 22 | n/a | Yes† | No | — |
| 8 | No | 19 | 64 | No | No | Myectomy |
| 9 | No | 13 | 0 | No | No | — |
| 10 | Yes | 17 | 16 | No | No | — |
| 11 | No | 18 | 112 | No | No | — |
| 12 | No | 15 | 140 | Yes* | No | — |
| 13 | No | 13 | 0 | Yes† | Yes (33, 59)† | — |
| 14 | No | 27 | 120 | No | No | Myectomy |
| 15 | No | 39 | 104 | No | No | PM, Myectomy |
| 16 | No | 24 | 48 | No | No | Myectomy |
| 17 | No | 23 | 0 | No | Yes (41)† | — |
| 18 | n/a | 19 | n/a | Yes* | No | — |
| 19 | n/a | 20 | 112 | Yes* | No | Myectomy |
| 20 | No | 21 | 52 | No | No | Myectomy |

AF, atrial fibrillation;
Dx, diagnosis;
FH, family history;
LVOTO, left ventricular outflow tract obstruction;
LVWT, left ventricular wall thickness;
n/a, information not available;
PM, pacemaker;
SCD, sudden cardiac death;
*, first degree relative;
†, second degree relative;
‡:1 = white-Caucasian; 2 = Hispanic Patients hosting a single ZASP mutation (cases 1 through 14) or a combination of a ZASP and a sarcomeric mutation (cases 15 through 20) had a clinical phenotype resembling that of the 228 patients who were genotype negative. The average age at diagnosis of patients hosting only a ZASP variant was 51.1±19 years, whereas patients hosting an additional sarcomeric mutation were diagnosed at 34.3±8 years of age (p=0.06).

Figure 2:
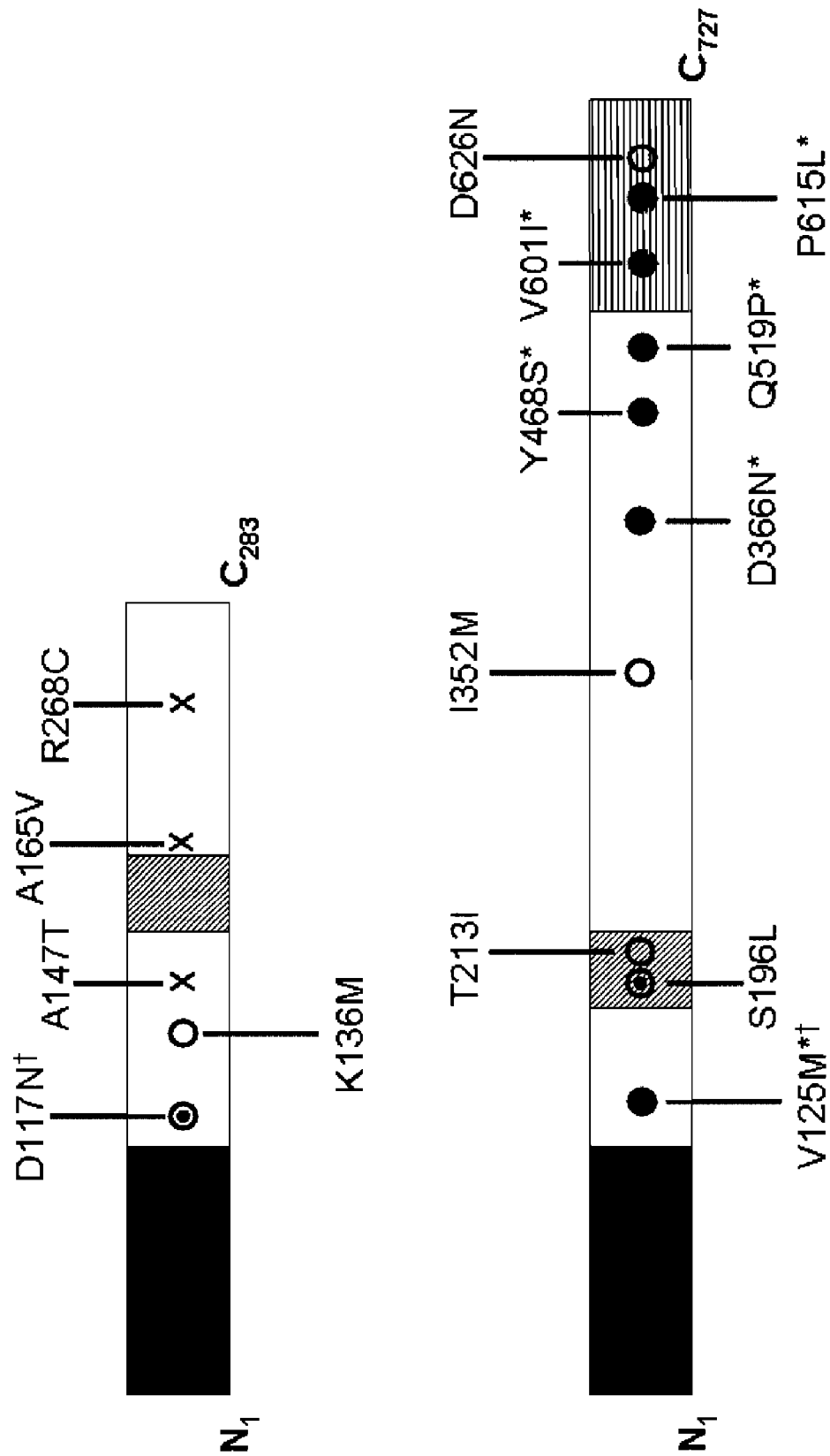
FIG. 2 is a schematic diagram of mutations found in HCM, DCM, LVNC, and MFM superimposed on the linear topology of ZASP. Open circles denote ZASP mutations found in patients with HCM, and closed circles represent mutations found in patients with DCM. A target symbol indicates mutations that have been found both in DCM and HCM patients, and mutations denoted with an "X" were recently identified in myofibrillar myopathy (MFM) patients. An asterisk denotes a newly identified mutation. Black rectangles represent PDZ domains, boxes with diagonal lines represent ZM-motifs, and the box with horizontal lines represents three LIM domains.
Figure 3:
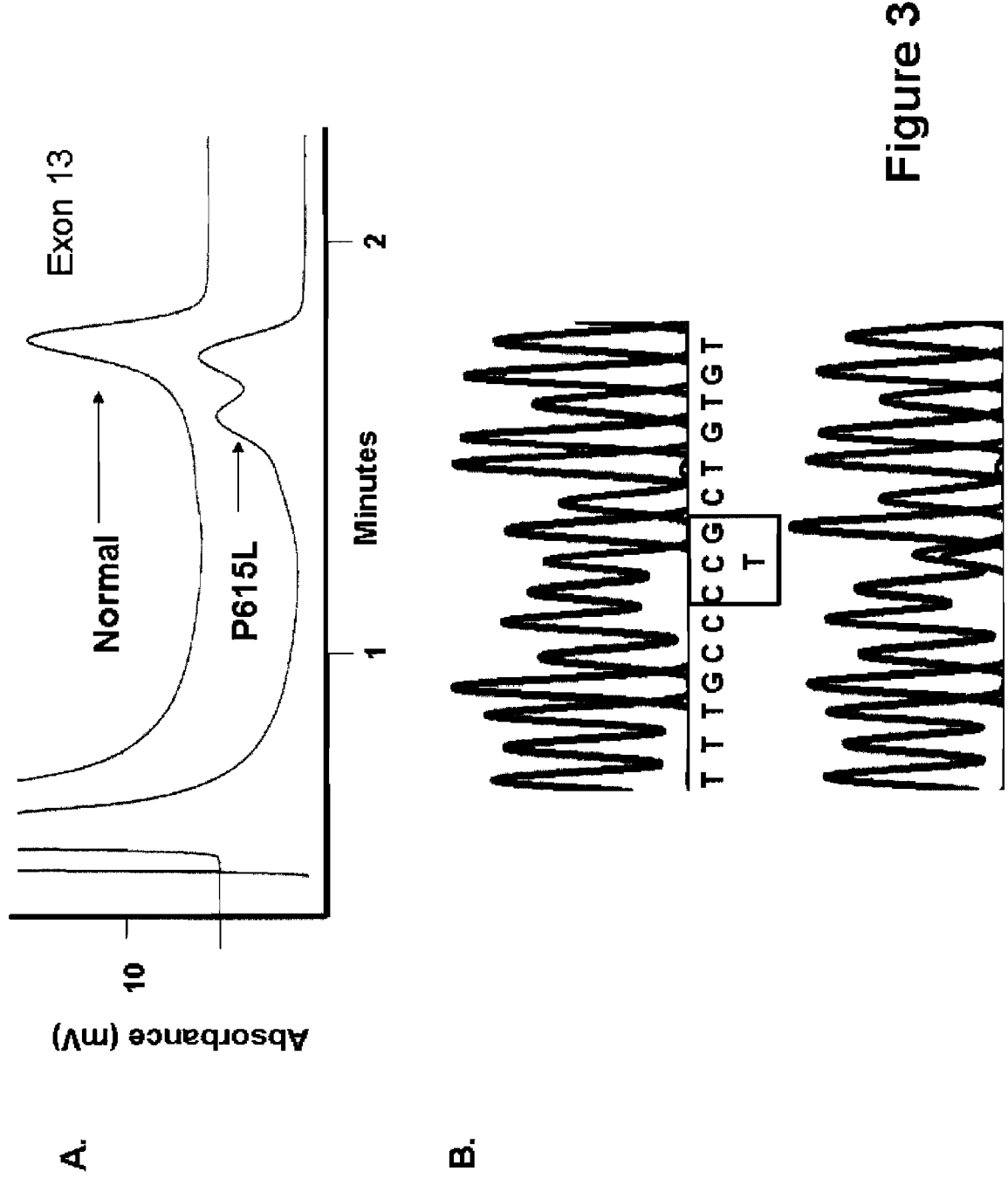
FIG. 3A is a graph plotting the DHPLC elution profile of a heterozygous amplicon from exon 13 of ZASP.
FIG. 3B contains sequence chromatograms of the wild-type and P615L alleles.
FIG. 3C is an alignment of orthologous ZASP sequences from the indicated species indicating conservation of proline at position 615SEQ ID NOS 105-111 respectively, in order of appearance).
FIG. 3D is a comparison of secondary structures of ZASP with leucine or proline at position 615, as predicted by PredictProtein (SEQ ID NOS 112-113 respectively, in order of appearance).

Overall, 11 distinct ZASP missense mutations, including nine newly identified mutations, were discovered (FIG. 2). These mutations were all non-conservative amino acid substitutions typically involving highly conserved residues across species. In silico analyses demonstrated significant disruption in secondary structure for each mutation. For example, a proline (P) to leucine (L) substitution at the highly conserved residue 615 (P615L-ZASP, FIG. 3A-C) was discovered in a 36-year-old male (case 14, Table 4) in whom no other mutations involving nine other HCM-associated sarcomeric nucleic acids were detected. The substitution was between the first two LIM domains and resulted in both the disruption of beta turns and the formation of alpha helices within this region (FIG. 3D). The patient had severe obstructive HCM with a maximal left ventricular wall thickness of 27 mm and a left ventricular outflow tract gradient of 120 mm Hg. A parasternal, long-axis view of an echocardiogram of a proband with P615L indicated marked hypertrophy involving the interventricular septum. Due to refractory symptoms in spite of medical therapy, the patient underwent a surgical myectomy. Microscopic evaluation of resected myocardium demonstrated myocyte hypertrophy with increased cell diameters and enlarged, hyperchromatic nuclei. A photomicrograph of a section of resected myocardium stained with hematoxylin and eosin (H & E) demonstrated myocyte hypertrophy with normal arrangement of myocytes having increased cell diameters and enlarged, hyperchromatic nuclei (Lamke et al., *Cardiovasc Pathol.* 12:149-58 (2003)).

Photomicrographs of immunofluorescent analyses detected strong ZASP staining at the Z-disc of control myocardium, and a dramatic overall reduction in the appearance of ZASP in myocardium obtained from the proband manifesting P615L. Phalloidin staining did not demonstrate a significant difference in Z-disk patterning or expression levels (original magnification 40×).

In addition to nine newly identified mutations, two mutations, D117N and S196L, were each found in two patients with HCM (Table 4, cases 1 and 15, and cases 8 and 9, respectively). These missense mutations were published previously as DCM/LVNC-associated mutations. In this study, however, S196L-ZASP was found in a patient (case 8) having apical variant-HCM with pronounced myocyte disarray. H & E staining of myectomy tissue from case 8 demonstrated marked myocyte disarray, showing haphazard arrangement of myocytes. S196 is conserved across species, and structural analyses predict that the introduction of S196L results in the ablation of both helices and beta turns N-terminal to the ZASP-like motif. S196L was not observed in 1020 reference alleles derived from 510 reportedly healthy subjects: 300 white, 100 black, and 110 Hispanic (Vatta et al., *J Am Coll Cardiol.* 42:2014-27 (2003)).

In addition to S196L, the previously published DCM/LVNC-associated variant, D117N, was also found in two patients with HCM (Table 4, cases 1 and 15). Parasternal, long-axis view of an echocardiogram of case 2 (D117N) illustrated marked septal hypertrophy. The histology was identified as a result of H & E staining illustrating myocyte disarray characterized by a "herringbone" arrangement of myocytes. This aspartate is conserved across species; however, this variant was also detected in 6% of the reference alleles from healthy blacks and 0.3% of the reference alleles from healthy whites. Secondary structure analysis for D117N indicated shortening of an alpha helix at position 228 of the C/Z1 isoform. The other reported DCM/LVNC-susceptibility variants (K136M, T213I, I352M, and D626N) were not observed in HCM cases or the additional 600 reference alleles examined (FIG. 2).

The non-synonymous variant, V125M, was identified in five of the 389 patients (i.e., >0.5% allelic frequency). Valine (V) at position 125 is invariant across species, except for the conservative substitution of alanine (A) in mouse and rat. Secondary structure analyses predicted ablation of a beta turn at position 124. Examination of over 1900 reference alleles revealed V125M in one healthy white control subject (p value<0.02; Table 4, cases 2-5 and 16).

The results established an association between ZASP mutations and HCM. More than five percent of unrelated patients with HCM hosted mutations in ZASP, making ZASP the third most common HCM-associated susceptibility nucleic acid.

Example 2

Identification of MYBPC3 Mutations in HCM Patients

A single institution cohort comprising 389 unrelated patients (215 male) was diagnosed with unequivocal and unexplained HCM at a mean age of 41.3±19 years. At presentation, 216 (55.5%) had cardiac symptoms, 120 (31%) had a family history of HCM, and 56 (14%) had a sudden cardiac death (SCD) event in a first-degree relative. The mean maximum left ventricular wall thickness (LVWT) was 21.5±7 mm, and mean peak gradient for left ventricular outflow tract obstruction (LVOTO) was 46.6±42 mm Hg. Of 389 patients, 297 (76%) had resting, labile, or mid-cavitary obstruction; 161 (41%) had undergone a surgical myectomy; and 60 (15%) had received an implantable cardioverter-defibrillator (ICD).

After providing written informed consent, the patients were enrolled in sarcomeric genetic testing. Patients were eligible for enrollment on the basis of 1) being seen and evaluated in the HCM clinic, 2) having an unequivocal diagnosis of HCM, and 3) being the first family member seen. By definition, each subject met the clinical diagnostic criteria for HCM by having a maximum LVWT greater than 13 mm in the absence of another confounding diagnosis.

Total genomic DNA was extracted from blood samples for subsequent mutational analysis using Purgene deoxyribonucleic acid (DNA) extraction kits (Gentra, Inc., Minneapolis, Minn.). This cohort was genotyped previously for mutations in nucleic acids encoding the sarcomeric polypeptides comprising the thick filament (MYH7 and the regulatory and essential light chains (MYL2 and MYL3)) and the thin filament (troponin-T (TNNT2), troponin-I (TNNI3), alpha-tropoinyosin (TPM1), and alpha-actin (ACTC); Van Driest et al., *Circulation* 108:445-51 (2003); Van Driest et al., *J Am Coll Cardiol* 44:602-10 (2004)).

PCR primers were designed to amplify all exons and flanking intronic sequences for each of the 34 polypeptide-coding exons of MYBPC3 (Table 5). Each exon of MYBPC3 was amplified in each patient's DNA sample, and amplicons were analyzed for sequence variants using denaturing high-performance liquid chromatography (DHPLC; WAVE, Transgenomic, Omaha, Nebr.; Underhill er al., *Genome Res* 7:996-1005 (1997)). All samples with abnormal DHPLC elution profiles were characterized by direct DNA sequencing (ABI Prism377; Applied Biosystems, Foster City, Calif.) to determine the precise sequence variation present. Nonsynonymous variants were confirmed by re-sequencing using stock DNA samples. DNA samples from 100 healthy blacks and 100 healthy whites (400 reference alleles) were obtained from Coriell Laboratories (Camden, N.J.) and tested for all candidate disease-associated mutations to confirm that none of the variants was a common polymorphism.

TABLE 5

MYBPC3 primers

| Exon | Forward Primer | Reverse Primer |
|---|---|---|
| 1 | TTGGGTGACCTGTGCCTG (SEQ ID NO:41) | CCCTGCTCCCACACTTAG (SEQ ID NO:42) |
| 2 | CGGGGTGCACGCTCCAA (SEQ ID NO:43) | CCAGCAGCCCAAACCTCA (SEQ ID NO:44) |
| 3 | GCGGGCTCATGGGTCCA (SEQ ID NO:45) | CCCAGCAAAGGCTTTTGA (SEQ ID NO:46) |
| 4 | GCCTGGGTGACAGAGCAA (SEQ ID NO:47) | CCTTCCCACCCCAATGCT (SEQ ID NO:48) |
| 5 | TGGCGAGGTGACCGTGG (SEQ ID NO:49) | CCTCTGTGTGCCTTGTGC (SEQ ID NO:50) |
| 6 | TTGTCTCCCGCCCCCTG (SEQ ID NO:51) | CCCGAGCCCAGGACAGA (SEQ ID NO:52) |
| 7-9 | AAGCCCCTTCCCCCATCTCT (SEQ ID NO:53) | CCAGCTGCCCCAGGAAC (SEQ ID NO:54) |
| 10 | GGTCGGCCCAACTGACTT (SEQ ID NO:55) | AGTCTCTCACCACAGCCT (SEQ ID NO:56) |
| 11 | ATGTGCCACCTACCCTTTC (SEQ ID NO:57) | GATGAGGGTGCTGTGCTAT (SEQ ID NO:58) |
| 12 | CCAGGGGCTGCAGTCT (SEQ ID NO:59) | CCTCTCCTCTCCTGTGTAG (SEQ ID NO:60) |
| 13 | CAGCCACAGCCACAGTAG (SEQ ID NO:61) | GGCAGGAGGCAAGGCTAT (SEQ ID NO:62) |
| 14 | TGCCGGTCCCTCTCTCTC (SEQ ID NO:63) | CAGGAAAGCTGCGGACAC (SEQ ID NO:64) |
| 15 | TCCGCAGCTTTCCTGCCA (SEQ ID NO:65) | CTCCCCTGAGGCCATCTC (SEQ ID NO:66) |
| 16-17 | GGGGAGCCAACCCTCATG (SEQ ID NO:67) | CAAGCCCTAAAGCCTCATGT (SEQ ID NO:68) |
| 18 | TCACGCCACACCCACACA (SEQ ID NO:69) | TCCATCTCAGTCTCCACCT (SEQ ID NO:70) |
| 19 | GGCTGGGGTATCTGGCAAG (SEQ ID NO:71) | CCGACCCACCCTACCCTG (SEQ ID NO:72) |
| 20 | CTGTCAGCCAAGCTCCACTTC (SEQ ID NO:73) | CCTTGCTCTTCCCTCTGTGAG (SEQ ID NO:74) |
| 21 | TCCCGTTTCTCTGAACTACA (SEQ ID NO:75) | CCACACACCCATCTTATAGA (SEQ ID NO:76) |
| 22 | AGCTCCTCTGCTCCCTAC (SEQ ID NO:77) | CGGCACCACGTAGGTAGA (SEQ ID NO:78) |
| 23 | CTCTGGGGTCTGACTTGG (SEQ ID NO:79) | GCTGCCCTCTGTGTTCT (SEQ ID NO:80) |
| 24 | GACGAGCAACGTTACTCAAG (SEQ ID NO:81) | ACCTTCCCTCGGATCTGTTT (SEQ ID NO:82) |
| 25 | GTTCCAGACCAGAGCTGC (SEQ ID NO:83) | TTAACTGGGGAGGGGCG (SEQ ID NO:84) |
| 26 | TTCCCCAGGCTTGCTCAG (SEQ ID NO:85) | ATGGCAAGGTGAGCATGTTC (SEQ ID NO:86) |
| 27 | TGGGAGTGGGGTGTCAGT (SEQ ID NO:87) | ACCTCCACTGGACACCAA (SEQ ID NO:88) |
| 28 | CGGGCCCTCACTTAGCTA (SEQ ID NO:89) | CCACTGGATGGGAACAAC (SEQ ID NO:90) |
| 29 | CATTTTCCAGTCCACTGC (SEQ ID NO:91) | CCAGGTTCAGGGTTAAGC (SEQ ID NO:92) |
| 30 | GGAGGCGTGGTGACCCAA (SEQ ID NO:93) | GTCCACGGTGAGGACAGTG (SEQ ID NO:94) |
| 31 | GAGGCTCTCGGCATCAGG (SEQ ID NO:95) | CTGTTGGTGACAGGACTTGGT (SEQ ID NO:96) |
| 32 | CTGTGGGAACAGGGAGAGG (SEQ ID NO:97) | GGAGAGGACTGCTCAACGTC (SEQ ID NO:98) |
| 33 | GTGTCTCCCTGGGTCCCT (SEQ ID NO:99) | CGAGGACAACGGAGCAAAG (SEQ ID NO:100) |
| 34 | CTTTGCTCCGTTGTCCTCG (SEQ ID NO:101) | CGCAGCACAGGAGACACACT (SEQ ID NO:102) |

Analysis of variance tests were used to assess differences between continuous variables, followed by Fisher Protected Least Significant Difference post-hoc testing for pairwise differences. Contingency tables or z-tests were used as appropriate to analyze nominal variables. Probability values less than 0.05 were considered statistically significant.

Figure 4:
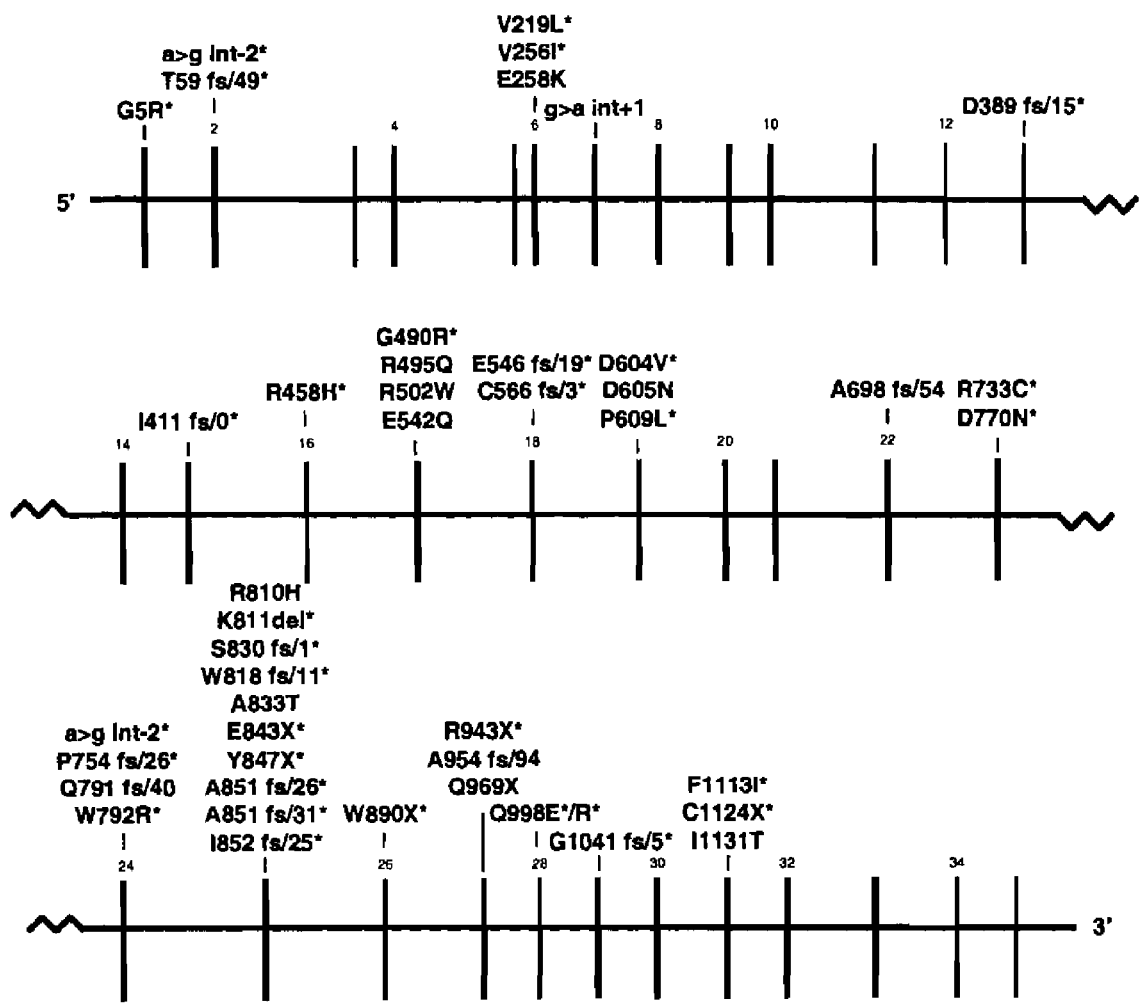
FIG. 4 is a schematic diagram of mutations identified in MYBPC3. Vertical lines represent exons, and mutations identified in this cohort are indicated above their exonic location. *Newly identified mutations.

In this cohort, 46 different MYBPC3 mutations were identified in 71 of 389 patients (18%). Eleven of the identified mutations were published previously, and the remaining 35 (72%) are newly identified mutations (Table 6; FIG. 4). Mutations were identified in 20 of 34 exons studied. None of the newly identified mutations were found in the 400 reference alleles. Twenty-one (46%) of the mutations identified altered single amino acids (missense mutations), 15 (33%) were insertions or deletions causing a frameshift, 6 (13%) coded for premature stop codons (nonsense mutations), 3 (7%) were putative splice donor or acceptor site mutations located in the introns, and 1 (2%) was an in-frame deletion (Table 6; FIG. 4). No statistically significant difference in clinical phenotype was attributable to the specific type of MYBPC3 mutation present (i.e., missense mutations versus premature truncations resulting from frameshift and nonsense mutations). In addition to the putative pathogenic mutations identified, 7 amino-acid altering variants in MYBPC3 were identified in patient samples as well as the 400 reference alleles (Table 6). In addition, three such variants (S236G, R326Q, and V896M) were identified in 5 patients, were not seen in the 400 reference alleles, but were previously reported as common polymorphisms with allele frequencies greater than 0.5% (Jaaskelainen et al., *J Mol Med* 80:412-22 (2002)). Therefore, these three variants were not considered pathogenic, and these five patients were not included in the MYBPC3-HCM subgroup.

TABLE 6

Putative HCM-Causing Mutations and Nonpathogenic, Nonsynonymous Polymorphisms Identified in MYBPC3

| Mutation or SNP # | Exon | Nucleotide Change | Variant | Mutation Type (Heterozygote Frequency for Polymorphisms)† |
|---|---|---|---|---|
| 1* | 1 | ggg > cgg | G5R | Missense mutation |
| 2* | 2 | a > g int − 2 | splice | Splice mutation |
| 3* | 2 | del gggcacacggc (SEQ ID NO: 103) | T59 fs/49 | Frameshift mutation |
| 4* | 6 | gtc > ctc | V219L | Missense mutation |
| 5* | 6 | gtc > atc | V256I | Missense mutation |
| 6 | 6 | gag > aag | E258K | Missense mutation |
| 7 | 7 | g > a int + 1 | splice | Splice mutation |
| 8* | 13 | del c | D389 fs/15 | Frameshift mutation |
| 9* | 15 | del tt | I411 fs/0 | Frameshift mutation |
| 10* | 16 | cgc > cag | R458H | Missense mutation |
| 11* | 17 | ggg > agg | G490R | Missense mutation |
| 12 | 17 | cgg > cag | R495Q | Missense mutation |
| 13 | 17 | cgg > tgg | R502W | Missense mutation |
| 14 | 17 | gaa > caa | E542Q | Missense mutation |
| 15* | 18 | del gt | E546 fs/19 | Frameshift mutation |
| 16* | 18 | del ga | C566 fs/3 | Frameshift mutation |
| 17* | 19 | gac > gtc | D604V | Missense mutation |
| 18* | 19 | gac > aac | D605N | Missense mutation |
| 19* | 19 | cct > ctt | P609L | Missense mutation |
| 20 | 22 | del c | A698 fs/54 | Frameshift mutation |
| 21* | 23 | cgc > tgc | R733C | Missense mutation |
| 22* | 23 | gac > aac | D770N | Missense mutation |
| 23* | 24 | a > g int − 2 | splice | Splice mutation |
| 24 | 24 | ins g | Q791 fs/40 | Frameshift mutation |
| 25* | 24 | tgg > cgg | W792R | Missense mutation |
| 26* | 24 | del g | P794 fs/26 | Frameshift mutation |
| 27 | 25 | cgc > cac | R810H | Missense mutation |
| 28* | 25 | del aag | K811del | Deletion mutation |
| 29* | 25 | del atgcg | WS 18 fs/11 | Frameshift mutation |
| 30* | 25 | ins t | S830 fs/1 | Frameshift mutation |
| 31 | 25 | gcg > acg | A833T | Missense mutation |
| 32* | 25 | gag > tag | E843X | Truncation mutation |
| 33* | 25 | tac > tag | Y847X | Truncation mutation |
| 34* | 25 | del c | A851 fs/26 | Frameshift mutation |
| 35* | 25 | ins t, ggc > tgc | A851 fs/31 | Frameshift mutation |
| 36* | 25 | del g | I852 fs/25 | Frameshift mutation |
| 37* | 26 | tgg > tga | W890X | Truncation mutation |
| 38* | 27 | cga > tga | R943X | Truncation mutation |
| 39 | 27 | del ct | A954 fs/94 | Frameshift mutation |
| 40 | 27 | caa > taa | Q969X | Truncation mutation |
| 41* | 28 | cag > gag | Q998E | Missense mutation |
| 42* | 28 | cag > cgg | Q998R | Missense mutation |
| 43* | 29 | ins aa | G1041 fs/5 | Frameshift mutation |
| 44* | 31 | ttc > atc | F1113I | Missense mutation |
| 45* | 31 | tgc > tga | C1124X | Truncation mutation |
| 46* | 31 | att > act | I1131T | Missense mutation |
| 1* | 4 | gtg > atg | V58M | Polymorphism (11%) |
| 2 | 6 | acg > ggc | S236G | Polymorphism (20%)‡ |
| 3 | 12 | cgg > cag | R326Q | Polymorphism (6%)‡ |
| 4* | 13 | cgg > tgg | R382W | Polymorphism (6%) |
| 5* | 15 | ggt > agt | G416S | Polymorphism (2%) |
| 6* | 17 | ggg > agg | G507R | Polymorphism (4%) |
| 7* | 18 | ctg > atg | L545M | Polymorphism (1%) |
| 8 | 26 | gtg > atg | V896M | Polymorphism (5%)‡ |
| 9 | 33 | cag > tag | Q1233X | Polymorphism (2%) |
| 10* | 33 | dup gggggcatctatgtctgc (SEQ ID NO: 104) | GGIYVC | Polymorphism (1%) |

*Indicates a newly identified mutation or variant;
†in 100 African American and 100 Caucasian DNA samples, unless otherwise noted;
‡previously published frequency (Jaaskelainen et al., J Mol Med 80: 412-22 (2002));
HCM = hypertrophic cardiomyopathy;
SNP = single nucleotide polymorphism.

Figure 5:
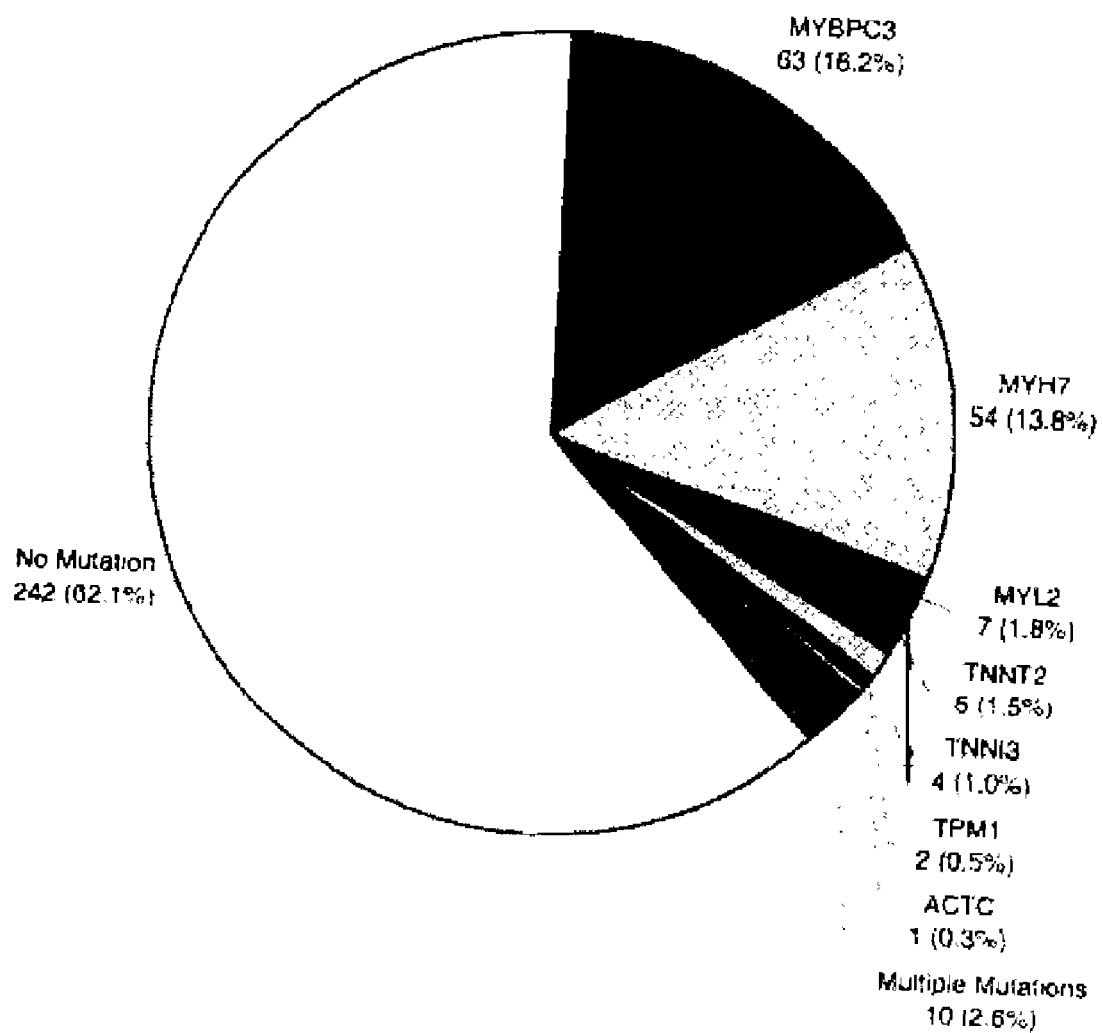
FIG. 5 is a pie chart indicating the distribution of sarcomeric mutations in patients with hypertrophic cardiomyopathy. The relative frequency of each genotype identified in the cohort of 389 unrelated patients is indicated as n (%). Each genotype is exclusive of patients with multiple mutations, who are included only in the "multiple mutations" subgroup.
Figure 6:
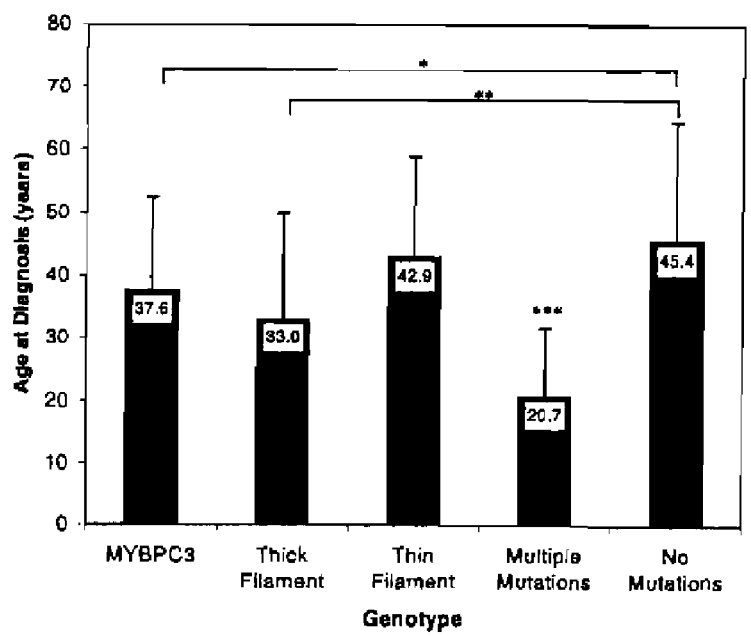
FIG. 6 is a graph plotting age at diagnosis of genotyped subsets. Genotyped hypertrophic cardiomyopathy patients are grouped on the X-axis, and age at diagnosis is indicated on the Y-axis. Error bars=standard deviation. Statistically significant pairwise comparisons are indicated. Thick filament=beta-myosin heavy chain and regulatory myosin light chain; thin filament=troponin-T, troponin-I, alpha-tropomyosin, and alpha-actin. *p=0.003;  p<0.0001; *p<0.05 versus all other subgroups.
Figure 7:
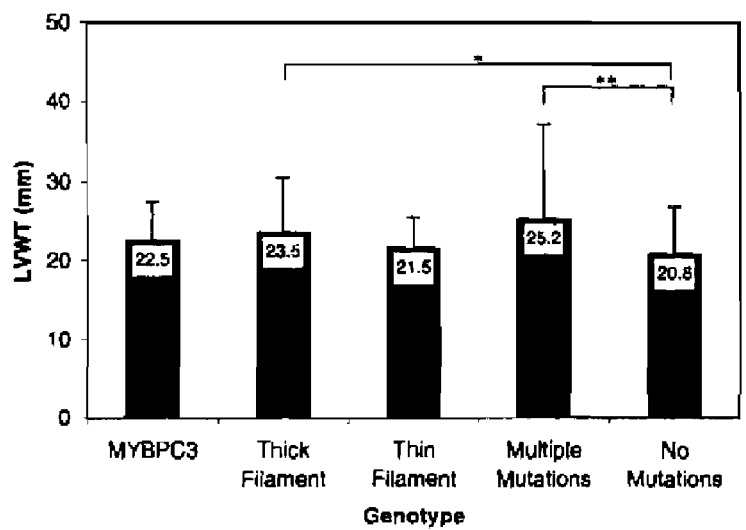
FIG. 7 is a graph plotting LVWT of genotyped subsets. Genotyped hypertrophic cardiomyopathy patients are grouped on the X-axis, and left ventricular wall thickness (LVWT) is indicated on the Y-axis. Error bars=standard deviation. Statistically significant pairwise comparisons are indicated. Thick filament=beta-myosin heavy chain and regulatory myosin light chain; thin filament=troponin-T, troponin-I, alpha-tropomyosin, and alpha-actin. *p=0.004; **p=0.03.

When patients with a single mutation in MYBPC3 (n=63, excluding those harboring multiple mutations in one or more nucleic acids; FIG. 5) were compared with patients with single mutations involving the thick filament (MYH7 or light chains, n=61), there were no statistically significant differences with respect to age at diagnosis (37.6±15 years versus 33.0±17 years), LVWT (22.5±5 mm versus 23.5±7 mm), frequency of myectomy (35% versus 56%), or frequency of ICD placement (29% versus 21%). These results are presented in Table 7. The phenotype ascribed to thick filament- HCM was not affected by removal of individuals with mutations in one of the two genetic components of the thick filament, namely mutations in the regulatory light chain encoded by MYL2. The same clinical parameters (age at diagnosis, LVWT, frequency of myectomy, and frequency of ICD placement) did not differ significantly between patients with thin filament mutations (alpha-actin, alphatropomyosin, troponin-T, or troponin-I; n=13) and patients with MYBPC3-HCM (Table 7; FIGS. 6 and 7). With regard to HCM morphology (resting obstruction, labile obstruction, mid-cavitary obstruction, apical, and nonobstructive HCM), again, there were no statistically significant differences between MYBPC3-HCM, thick filament-HCM, thin filament-HCM, and multiple mutation-HCM patients.

6). In fact, patients with genotype-negative HCM were even older at diagnosis than those with MYBPC3-HCM (45.4±19 years vs. 37.6±15 years, p<0.003). The genotype-negative patients also had significantly less hypertrophy than patients with thick filament or multiple mutations. In addition, there was a trend toward less hypertrophy in genotype-negative patients than in patients with MYBPC3-HCM (Table 7; FIG. 7).

Ten of 389 patients (2.6% of the total cohort; 7% of the genotyped subset) were identified as having multiple sarcomeric mutations, i.e., compound heterozygosity (FIG. 5). One patient had mutations in MYH7 and troponin-T (R453C and Q191del, respectively). Another patient had two MYH7 mutations (R719Q plus T1513S). Multiple MYBPC3 muta-

TABLE 7

Clinical characteristics of patients with single, multiple, or no sarcomeric mutations

| | MYBPC3 Mutation | Thick Filament Mutation | Thin Filament Mutation | Multiple Mutations | No Sarcomeric Mutation | ANOVA p Value |
|---|---|---|---|---|---|---|
| Number of individuals | 63 | 61 | 13 | 10 | 242 | |
| Male/female | 41/22 | 25/36 | 10/3 | 5/5 | 134/108 | 0.04 |
| Age at diagnosis | | | | | | |
| Mean | 37.6 ± 15 | 33.0 ± 17 | 42.9 ± 16 | 20.7 ± 11 | 45.4 ± 19 | <0.0001 |
| Range | 3.4-75.2 | 0.1-70.6 | 22.6-72.5 | 0.2-37.4 | 0.0-89.5 | |
| >25 yrs, n (%) | 50 (79%) | 41 (67%) | 12 (92%) | 3 (30%) | 202 (83%) | <0.0001 |
| Presentation | | | | | | |
| Cardiac symptoms, n (%) | 37 (59%) | 30 (49%) | 10 (77%) | 4 (40%) | 134 (55%) | 0.08 |
| Family history* | | | | | | |
| HCM, n (%) | 28 (44%) | 27 (44%) | 5 (38%) | 5 (50%) | 55 (23%) | 0.01 |
| SCD, n (%) | 13 (21%) | 11 (18%) | 3 (23%) | 2 (20%) | 27 (11%) | 0.35 |
| Echocardiography | | | | | | |
| LVWT (mm) | 22.5 ± 5 | 23.5 ± 7 | 21.5 ± 4 | 25.2 ± 12 | 20.8 ± 6 | 0.01 |
| Severe hypertrophy†, n (%) | 4 (6%) | 9 (15%) | 0 (0%) | 2 (20%) | 14 (6%) | 0.07 |
| Peak LVOT gradient (mm Hg) | 41.4 ± 38 | 52.3 ± 46 | 34.9 ± 42 | 46.3 ± 44 | 47.3 ± 42 | 0.60 |
| >30 mm Hg at rest, n (%) | 31 (49%) | 36 (59%) | 5 (38%) | 6 (60%) | 128 (53%) | 0.79 |
| Treatment | | | | | | |
| Myotomy/myectomy, n (%) | 22 (35%) | 34 (56%) | 3 (23%) | 6 (60%) | 95 (39%) | 0.04 |
| PM, n (%) | 12 (19%) | 13 (21%) | 2 (15%) | 0 (0%) | 40 (17%) | 0.55 |
| Myectomy or PM, n (%) | 25 (40%) | 37 (61%) | 4 (31%) | 6 (60%) | 117 (48%) | 0.10 |
| ICD, n (%) | 18 (29%) | 13 (21%) | 2 (15%) | 4 (40%) | 23 (10%) | 0.003 |

No significant differences were defined between MYBPC3-HCM and thick filament-HCM subsets.
*In a first degree relative;
†LVWT ≥ 30 mm;
ANOVA = analysis of variance;
HCM = hypertrophic cardiomyopathy;
ICD = implantable cardioverter-defibrillator;
LVOT = left ventricular outflow tract;
LVWT = left ventricular wall thickness;
MYBPC3 = myosin binding protein C;
PM = permanent pacemaker;
SCD = sudden cardiac death;
thick filament = β-myosin heavy chain and regulatory myosin light chain;
thin filament = troponin-T, troponin-I, α-tropomyosin, and α-actin.

Of the 389 patients, 242 (62.2%) had no mutations in MYH7, MYL2, MYL3, TNNT2, TNNI3, TPM1, ACTC, or MYBPC3. This genotype negative subset of patients was significantly older at diagnosis than genotype positive patients with an identifiable sarcomere defect (Table 7; FIG.

tions were identified in two patients (G5R plus R502W, E258K plus A954fs/94). Two patients had mutations in MYBPC3 and MYH7 (D605N plus E894G, Q791fs/40 plus R694C). MYBPC3 and troponin-T mutations (V256I plus R92W, A833T plus R286H) also were identified in two patients. MYBPC3 and troponin-I mutations were identified in one patient (R943X plus S166F). Another patient had mutations in MYBPC3 and α-tropomyosin (F1113I plus I172T). These 10 patients were significantly younger at diagnosis than any other subgroup, had the most hypertrophy, and had the highest incidence of myectomy and ICD placement, three out of four of which were placed due to a strong family history of SCD (Table 7, FIGS. 6 and 7).

These results indicated that patients with MYBPC3 mutations did not differ significantly from patients with thick filament-HCM, thin filament-HCM, or genotype-negative HCM with respect to age at diagnosis, degree of hypertrophy, incidence of myectomy, or family history of HCM or sudden death. Patients with multiple mutations had the most severe disease presentation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining a human's susceptibility to develop hypertrophic cardiomyopathy, said method comprising determining whether or not a human comprises genomic MYBPC3 nucleic acid comprising one or more mutations selected from the group consisting of mutation nos. 1-5, 9-11, 15-19, 21-23, 25, 26, 29, 30, 32-38, 42, and 44-46 as listed in Table 6, wherein the presence of said one or more mutations indicates that said human is susceptible to develop hypertrophic cardiomyopathy.

2. The method of claim 1, wherein said determining step comprises analyzing DNA.

3. The method of claim 1, wherein said determining step comprises analyzing RNA.

4. The method of claim 1, wherein said determining step comprises analyzing a polypeptide sample.

5. The method of claim 1, wherein said determining step comprises analyzing a blood sample from said human.

6. A method for determining whether or not a human comprises one or more MYBPC3 mutations selected from the group consisting of mutation nos. 1-5, 9-11, 15-19, 21-23, 25, 26, 29, 30, 32-38, 42, and 44-46 as listed in Table 6, said method comprising analyzing a biological sample from said human for the presence or absence of said one or more MYBPC3 mutations using polymerase chain reaction, denaturing high-performance liquid chromatography, or sequencing.

7. The method of claim 6, wherein said sample is blood.

8. The method of claim 6, wherein said sample is genomic DNA.

9. An amplification product comprising an MYBPC3 nucleic acid molecule less than 2500 nucleotides in length, wherein said nucleic acid molecule comprises one or more MYBPC3 mutations selected from the group consisting of mutation nos. 1-5, 9-11, 15-19, 21-23, 25, 26, 29, 30, 32-38, 42, and 44-46 as listed in Table 6, wherein said amplification product is at least 50% pure for said nucleic acid molecule.

10. An isolated polynucleotide having the ability to hybridize to a first MYBPC3 nucleic acid molecule comprising a mutation selected from the group consisting of mutation nos. 1-5, 9-11, 15-19, 21-23, 25, 26, 29, 30, 32-38, 42, and 44-46 as listed in Table 6 under hybridization conditions and not having the ability to hybridize to a second MYBPC3 nucleic acid molecule not comprising said mutation under the same hybridization conditions.

11. The polynucleotide of claim 10, wherein said polynucleotide comprises a fluorescent or radioactive label.

12. The method of claim 1, wherein said method comprises diagnosing said human as having an elevated risk of developing hypertrophic cardiomyopathy if said human has said one or more mutations, and wherein said method comprises not diagnosing said human as having an elevated risk of developing hypertrophic cardiomyopathy if said human does not have said one or more mutations.

* * * * *

SEQUENCE LISTING

```
<160> NUMBER OF SEQ ID NOS: 113

<210> SEQ ID NO 1
<211> LENGTH: 1020
<212> TYPE: DNA
<213> ORGANISM: Homo sapiens
<220> FEATURE:
<221> NAME/KEY: CDS
<222> LOCATION: (80)..(928)

<400> SEQUENCE: 1
gcaggcggag tgcctgagtg ccctctcact caaccctctc taccctttgt ctgcagaggc    60
ggccgctgac agcaccagc atg tct tac agt gtg acc ctg act ggg ccc ggg    112
                     Met Ser Tyr Ser Val Thr Leu Thr Gly Pro Gly
                       1               5                      10 ccc tgg ggc ttc cgt ctg cag ggg ggc aag gac ttc aac atg ccc ctc    160
Pro Trp Gly Phe Arg Leu Gln Gly Gly Lys Asp Phe Asn Met Pro Leu
             15                  20                  25 act atc tcc cgg atc aca cca ggc agc aag gca gcc cag tcc cag ctc    208
Thr Ile Ser Arg Ile Thr Pro Gly Ser Lys Ala Ala Gln Ser Gln Leu
         30                  35                  40 agc cag ggt gac ctc gtg gtg gcc att gac ggc gtc aac aca gac acc    256
Ser Gln Gly Asp Leu Val Val Ala Ile Asp Gly Val Asn Thr Asp Thr
     45                  50                  55 atg acc cac ctg gaa gcc cag aac aag atc aag tct gcc agc tac aac    304
Met Thr His Leu Glu Ala Gln Asn Lys Ile Lys Ser Ala Ser Tyr Asn
 60                  65                  70                  75 ttg agc ctc acc ctg cag aaa tca aag cgt ccc att ccc atc tcc acg    352
Leu Ser Leu Thr Leu Gln Lys Ser Lys Arg Pro Ile Pro Ile Ser Thr
                 80                  85                  90 aca gca cct cca gtc cag acc cct ctg ccg gtg atc cct cac cag aag    400
Thr Ala Pro Pro Val Gln Thr Pro Leu Pro Val Ile Pro His Gln Lys
             95                 100                 105 gta gcc agc ccc gag ccc atg agc gcc gac tac cag gaa cgc ttc aac    448
Val Ala Ser Pro Glu Pro Met Ser Ala Asp Tyr Gln Glu Arg Phe Asn
        110                 115                 120 ccc agt gcc ctg aag gac tcg gcc ctg tcc acc cac aag ccc atc gag    496
Pro Ser Ala Leu Lys Asp Ser Ala Leu Ser Thr His Lys Pro Ile Glu
    125                 130                 135 gtg aag ggg ctg ggc ggc aag gcc acc atc atc cat gcg cag tac aac    544
Val Lys Gly Leu Gly Gly Lys Ala Thr Ile Ile His Ala Gln Tyr Asn
140                 145                 150                 155 acg ccc atc agc atg tat tcc cag gat gcc atc atg gat gcc atc gct    592
Thr Pro Ile Ser Met Tyr Ser Gln Asp Ala Ile Met Asp Ala Ile Ala
                160                 165                 170 ggg cag gcc caa gcc caa ggc agt gac ttc agt ggg agc ctc cct att    640
Gly Gln Ala Gln Ala Gln Gly Ser Asp Phe Ser Gly Ser Leu Pro Ile
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 175 |     |     |     | 180 |     |     |     | 185 |     |     |     |     |      |
| aag | gac | ctt | gcc | gta | gac | agc | gcc | tct | ccc | gtc | tac | cag | gct | gtg | att | 688  |
| Lys | Asp | Leu | Ala | Val | Asp | Ser | Ala | Ser | Pro | Val | Tyr | Gln | Ala | Val | Ile |      |
|     |     | 190 |     |     |     | 195 |     |     |     | 200 |     |     |     |     |     |      |
| aag | agc | cag | aac | aag | cca | gaa | gat | gag | gct | gac | gag | tgg | gca | cgc | cgt | 736  |
| Lys | Ser | Gln | Asn | Lys | Pro | Glu | Asp | Glu | Ala | Asp | Glu | Trp | Ala | Arg | Arg |      |
|     | 205 |     |     |     | 210 |     |     |     | 215 |     |     |     |     |     |     |      |
| tcc | tcc | aac | ctg | cag | tct | cgc | tcc | ttc | cgc | atc | ctg | gcc | cag | atg | acg | 784  |
| Ser | Ser | Asn | Leu | Gln | Ser | Arg | Ser | Phe | Arg | Ile | Leu | Ala | Gln | Met | Thr |      |
| 220 |     |     |     | 225 |     |     |     | 230 |     |     |     | 235 |     |     |     |      |
| ggg | aca | gaa | ttc | atg | caa | gac | cct | gat | gaa | gaa | gct | ctg | cga | agg | tca | 832  |
| Gly | Thr | Glu | Phe | Met | Gln | Asp | Pro | Asp | Glu | Glu | Ala | Leu | Arg | Arg | Ser |      |
|     |     |     | 240 |     |     |     | 245 |     |     |     | 250 |     |     |     |     |      |
| agg | gaa | agg | ttt | gaa | acg | gaa | cgt | aac | agc | cca | cgt | ttt | gcc | aaa | ttg | 880  |
| Arg | Glu | Arg | Phe | Glu | Thr | Glu | Arg | Asn | Ser | Pro | Arg | Phe | Ala | Lys | Leu |      |
|     |     | 255 |     |     |     | 260 |     |     |     | 265 |     |     |     |     |     |      |
| cgc | aac | tgg | cac | cat | ggc | ctt | tca | gcc | caa | atc | ctt | aat | gtt | aaa | agc | 928  |
| Arg | Asn | Trp | His | His | Gly | Leu | Ser | Ala | Gln | Ile | Leu | Asn | Val | Lys | Ser |      |
|     | 270 |     |     |     | 275 |     |     |     | 280 |     |     |     |     |     |     |      |
| taaaaggctg | | cctggaatcc | | ccccacccca | | acaggctgga | | ctccctccat | | ccttaccccc | | | | | | 988 |
| acacagatct | | ggcatgtgag | | ccccacggtg | | at | | | | | | | | | | 1020 |

<210> SEQ ID NO 2
<211> LENGTH: 283
<212> TYPE: PRT
<213> ORGANISM: Homo sapiens

<400> SEQUENCE: 2

Met Ser Tyr Ser Val Thr Leu Thr Gly Pro Gly Pro Trp Gly Phe Arg
  1               5                  10                  15

Leu Gln Gly Gly Lys Asp Phe Asn Met Pro Leu Thr Ile Ser Arg Ile
                 20                  25                  30

Thr Pro Gly Ser Lys Ala Ala Gln Ser Gln Leu Ser Gln Gly Asp Leu
             35                  40                  45

Val Val Ala Ile Asp Gly Val Asn Thr Asp Thr Met Thr His Leu Glu
         50                  55                  60

Ala Gln Asn Lys Ile Lys Ser Ala Ser Tyr Asn Leu Ser Leu Thr Leu
 65                  70                  75                  80

Gln Lys Ser Lys Arg Pro Ile Pro Ile Ser Thr Thr Ala Pro Pro Val
                 85                  90                  95

Gln Thr Pro Leu Pro Val Ile Pro His Gln Lys Val Ala Ser Pro Glu
            100                 105                 110

Pro Met Ser Ala Asp Tyr Gln Glu Arg Phe Asn Pro Ser Ala Leu Lys
            115                 120                 125

Asp Ser Ala Leu Ser Thr His Lys Pro Ile Glu Val Lys Gly Leu Gly
        130                 135                 140

Gly Lys Ala Thr Ile Ile His Ala Gln Tyr Asn Thr Pro Ile Ser Met
145                 150                 155                 160

Tyr Ser Gln Asp Ala Ile Met Asp Ala Ile Ala Gly Gln Ala Gln Ala
                165                 170                 175

Gln Gly Ser Asp Phe Ser Gly Ser Leu Pro Ile Lys Asp Leu Ala Val
            180                 185                 190

Asp Ser Ala Ser Pro Val Tyr Gln Ala Val Ile Lys Ser Gln Asn Lys
        195                 200                 205

Pro Glu Asp Glu Ala Asp Glu Trp Ala Arg Arg Ser Ser Asn Leu Gln
    210                 215                 220

```
Ser Arg Ser Phe Arg Ile Leu Ala Gln Met Thr Gly Thr Glu Phe Met
225                 230                 235                 240

Gln Asp Pro Asp Glu Glu Ala Leu Arg Arg Ser Arg Glu Arg Phe Glu
            245                 250                 255

Thr Glu Arg Asn Ser Pro Arg Phe Ala Lys Leu Arg Asn Trp His His
        260                 265                 270

Gly Leu Ser Ala Gln Ile Leu Asn Val Lys Ser
        275                 280

<210> SEQ ID NO 3
<211> LENGTH: 2220
<212> TYPE: DNA
<213> ORGANISM: Homo sapiens
<220> FEATURE:
<221> NAME/KEY: CDS
<222> LOCATION: (22)..(2202)

<400> SEQUENCE: 3
gcggccgctg acagcaccag c atg tct tac agt gtg acc ctg act ggg ccc      51
                       Met Ser Tyr Ser Val Thr Leu Thr Gly Pro
                         1               5                  10 ggg ccc tgg ggc ttc cgt ctg cag ggg ggc aag gac ttc aac atg ccc      99
Gly Pro Trp Gly Phe Arg Leu Gln Gly Gly Lys Asp Phe Asn Met Pro
             15                  20                  25 ctc act atc tcc cgg atc aca cca ggc agc aag gca gcc cag tcc cag     147
Leu Thr Ile Ser Arg Ile Thr Pro Gly Ser Lys Ala Ala Gln Ser Gln
         30                  35                  40 ctc agc cag ggt gac ctc gtg gtg gcc att gac ggc gtc aac aca gac     195
Leu Ser Gln Gly Asp Leu Val Val Ala Ile Asp Gly Val Asn Thr Asp
     45                  50                  55 acc atg acc cac ctg gaa gcc cag aac aag atc aag tct gcc agc tac     243
Thr Met Thr His Leu Glu Ala Gln Asn Lys Ile Lys Ser Ala Ser Tyr
 60                  65                  70 aac ttg agc ctc acc ctg cag aaa tca aag cgt ccc att ccc atc tcc     291
Asn Leu Ser Leu Thr Leu Gln Lys Ser Lys Arg Pro Ile Pro Ile Ser
 75                  80                  85                  90 acg aca gca cct cca gtc cag acc cct ctg ccg gtg atc cct cac cag     339
Thr Thr Ala Pro Pro Val Gln Thr Pro Leu Pro Val Ile Pro His Gln
                 95                 100                 105 aag gac ccc gct ctg gac acg aac ggc agc ctg gtg gca ccc agc ccc     387
Lys Asp Pro Ala Leu Asp Thr Asn Gly Ser Leu Val Ala Pro Ser Pro
             110                 115                 120 agc cct gag gcg agg gcc agc cca ggc acc cca ggc acc ccg gag ctc     435
Ser Pro Glu Ala Arg Ala Ser Pro Gly Thr Pro Gly Thr Pro Glu Leu
         125                 130                 135 agg ccc acc ttt agc cct gcc ttc tcc cgg ccc tcc gcc ttc tcc tca     483
Arg Pro Thr Phe Ser Pro Ala Phe Ser Arg Pro Ser Ala Phe Ser Ser
     140                 145                 150 ctc gcc gag gcc tct gac cct ggc cct ccg cgg gcc agc ctg agg gcc     531
Leu Ala Glu Ala Ser Asp Pro Gly Pro Pro Arg Ala Ser Leu Arg Ala
155                 160                 165                 170 aag acc agc cca gag ggg gcc cgg gac cta ctc ggc cca aaa gcc ctg     579
Lys Thr Ser Pro Glu Gly Ala Arg Asp Leu Leu Gly Pro Lys Ala Leu
                175                 180                 185 ccg ggc tcg agc cag ccg agg caa tat aac aac ccc att ggc ctg tac     627
Pro Gly Ser Ser Gln Pro Arg Gln Tyr Asn Asn Pro Ile Gly Leu Tyr
            190                 195                 200 tcg gca gag acc ctg agg gag atg gct cag atg tac cag atg agc ctc     675
Ser Ala Glu Thr Leu Arg Glu Met Ala Gln Met Tyr Gln Met Ser Leu
        205                 210                 215
```

```
cga ggg aag gcc tcg ggt gtc gga ctc cca gga ggg agc ctc cct att      723
Arg Gly Lys Ala Ser Gly Val Gly Leu Pro Gly Gly Ser Leu Pro Ile
    220             225             230 aag gac ctt gcc gta gac agc gcc tct ccc gtc tac cag gct gtg att      771
Lys Asp Leu Ala Val Asp Ser Ala Ser Pro Val Tyr Gln Ala Val Ile
235             240             245             250 aag agc cag aac aag cca gaa gat gag gct gac gag tgg gca cgc cgt      819
Lys Ser Gln Asn Lys Pro Glu Asp Glu Ala Asp Glu Trp Ala Arg Arg
                255             260             265 tcc tcc aac ctg cag tct cgc tcc ttc cgc atc ctg gcc cag atg acg      867
Ser Ser Asn Leu Gln Ser Arg Ser Phe Arg Ile Leu Ala Gln Met Thr
        270             275             280 ggg aca gaa ttc atg caa gac cct gat gaa gaa gct ctg cga agg tca      915
Gly Thr Glu Phe Met Gln Asp Pro Asp Glu Glu Ala Leu Arg Arg Ser
    285             290             295 agc acc cct att gag cat gcg ccg gtg tgc acc agc cag gcc acc acc      963
Ser Thr Pro Ile Glu His Ala Pro Val Cys Thr Ser Gln Ala Thr Thr
300             305             310 ccg ctg ctg ccc gct tct gcc cag cca cct gct gct gcc tct ccc agt     1011
Pro Leu Leu Pro Ala Ser Ala Gln Pro Pro Ala Ala Ala Ser Pro Ser
315             320             325             330 gcg gct tcg cca ccc ctg gcc aca gct gct gcc cac act gcc atc gcc     1059
Ala Ala Ser Pro Pro Leu Ala Thr Ala Ala Ala His Thr Ala Ile Ala
                335             340             345 tcc gcc tcc acc aca gcc cct gct tca agt cct gcc gac agc cca agg     1107
Ser Ala Ser Thr Thr Ala Pro Ala Ser Ser Pro Ala Asp Ser Pro Arg
        350             355             360 ccc cag gcc tct tcc tac agc ccc gca gtg gcc gcc tct tca gca cct     1155
Pro Gln Ala Ser Ser Tyr Ser Pro Ala Val Ala Ala Ser Ser Ala Pro
    365             370             375 gcc acc cac acc agc tac agt gag ggc ccc gcc gcc cct gca ccc aag     1203
Ala Thr His Thr Ser Tyr Ser Glu Gly Pro Ala Ala Pro Ala Pro Lys
380             385             390 ccc cgg gtt gtc acc act gcc agc atc cgg cct tct gtc tac cag cca     1251
Pro Arg Val Val Thr Thr Ala Ser Ile Arg Pro Ser Val Tyr Gln Pro
395             400             405             410 gtg cct gca tct acc tac agc ccg tcc cca ggg gcc aat tac agt ccc     1299
Val Pro Ala Ser Thr Tyr Ser Pro Ser Pro Gly Ala Asn Tyr Ser Pro
                415             420             425 act ccc tac acc ccc tcc cct gcc cct gcc tac acc ccc tcc cct gcc     1347
Thr Pro Tyr Thr Pro Ser Pro Ala Pro Ala Tyr Thr Pro Ser Pro Ala
        430             435             440 cct gcc tac acc ccc tca cct gtc ccc acc tac act cca tcc cca gca     1395
Pro Ala Tyr Thr Pro Ser Pro Val Pro Thr Tyr Thr Pro Ser Pro Ala
    445             450             455 cca gcc tat acc ccc tca cct gcc ccc aac tat aac cct gca ccc tcg     1443
Pro Ala Tyr Thr Pro Ser Pro Ala Pro Asn Tyr Asn Pro Ala Pro Ser
460             465             470 gtg gcc tac agc ggg ggc cct gcg gag cct gcc agc cgt cca ccc tgg     1491
Val Ala Tyr Ser Gly Gly Pro Ala Glu Pro Ala Ser Arg Pro Pro Trp
475             480             485             490 gtg aca gat gat agc ttc tcc cag aag ttt gcc ccg ggc aag agc acc     1539
Val Thr Asp Asp Ser Phe Ser Gln Lys Phe Ala Pro Gly Lys Ser Thr
                495             500             505 acc tcc atc agc aag cag acc ctg ccc cgg gga ggc cca gcc tac acc     1587
Thr Ser Ile Ser Lys Gln Thr Leu Pro Arg Gly Gly Pro Ala Tyr Thr
        510             515             520 cca gcg ggt cct cag gtg cca cca ctt gcc agg ggg acc gtc cag agg     1635
Pro Ala Gly Pro Gln Val Pro Pro Leu Ala Arg Gly Thr Val Gln Arg
```

-continued

```
                525                 530                 535
gct gag cga ttc cca gcc agc agc cgg act cca ctc tgc ggt cac tgc      1683
Ala Glu Arg Phe Pro Ala Ser Ser Arg Thr Pro Leu Cys Gly His Cys
540                 545                 550 aac aat gtc atc cgg ggc cca ttt ctg gta gcc atg ggc cgt tct tgg      1731
Asn Asn Val Ile Arg Gly Pro Phe Leu Val Ala Met Gly Arg Ser Trp
555                 560                 565                 570 cac cct gaa gag ttc acc tgt gcc tac tgc aag act tcc ctg gca gat      1779
His Pro Glu Glu Phe Thr Cys Ala Tyr Cys Lys Thr Ser Leu Ala Asp
                575                 580                 585 gtg tgc ttt gtg gaa gag cag aac aac gtt tac tgt gag cga tgt tat      1827
Val Cys Phe Val Glu Glu Gln Asn Asn Val Tyr Cys Glu Arg Cys Tyr
            590                 595                 600 gag caa ttc ttt gcc ccg ctg tgt gcc aag tgc aac acc aaa att atg      1875
Glu Gln Phe Phe Ala Pro Leu Cys Ala Lys Cys Asn Thr Lys Ile Met
        605                 610                 615 ggg gaa gta atg cat gcc ttg aga cag aca tgg cac acc acc tgc ttc      1923
Gly Glu Val Met His Ala Leu Arg Gln Thr Trp His Thr Thr Cys Phe
620                 625                 630 gtc tgt gcg gcc tgc aag aag cct ttt ggg aac agc ctc ttc cac atg      1971
Val Cys Ala Ala Cys Lys Lys Pro Phe Gly Asn Ser Leu Phe His Met
635                 640                 645                 650 gaa gac ggg gag ccc tac tgc gag aaa gac tac atc aat ctg ttc agc      2019
Glu Asp Gly Glu Pro Tyr Cys Glu Lys Asp Tyr Ile Asn Leu Phe Ser
                655                 660                 665 acc aag tgc cat ggc tgc gat ttc ccc gtg gag gct ggc gac aag ttt      2067
Thr Lys Cys His Gly Cys Asp Phe Pro Val Glu Ala Gly Asp Lys Phe
            670                 675                 680 atc gaa gcc ctg ggc cac act tgg cac gac acc tgc ttc att tgc gca      2115
Ile Glu Ala Leu Gly His Thr Trp His Asp Thr Cys Phe Ile Cys Ala
        685                 690                 695 gtc tgc cat gtg aat ctg gag ggg cag ccg ttc tac tcc aag aag gac      2163
Val Cys His Val Asn Leu Glu Gly Gln Pro Phe Tyr Ser Lys Lys Asp
700                 705                 710 aga ccc ctg tgc aag aag cac gca cac acc atc aac ttg taggcggcca      2212
Arg Pro Leu Cys Lys Lys His Ala His Thr Ile Asn Leu
715                 720                 725 aggccgcc                                                              2220
```

<210> SEQ ID NO 4
<211> LENGTH: 727
<212> TYPE: PRT
<213> ORGANISM: Homo sapiens

<400> SEQUENCE: 4

```
Met Ser Tyr Ser Val Thr Leu Thr Gly Pro Gly Pro Trp Gly Phe Arg
 1               5                  10                  15

Leu Gln Gly Gly Lys Asp Phe Asn Met Pro Leu Thr Ile Ser Arg Ile
            20                  25                  30

Thr Pro Gly Ser Lys Ala Ala Gln Ser Gln Leu Ser Gln Gly Asp Leu
        35                  40                  45

Val Val Ala Ile Asp Gly Val Asn Thr Asp Thr Met Thr His Leu Glu
    50                  55                  60

Ala Gln Asn Lys Ile Lys Ser Ala Ser Tyr Asn Leu Ser Leu Thr Leu
65                  70                  75                  80

Gln Lys Ser Lys Arg Pro Ile Pro Ile Ser Thr Thr Ala Pro Pro Val
                85                  90                  95

Gln Thr Pro Leu Pro Val Ile Pro His Gln Lys Asp Pro Ala Leu Asp
```

-continued

```
                100                 105                 110
Thr Asn Gly Ser Leu Val Ala Pro Ser Pro Ser Pro Glu Ala Arg Ala
            115                 120                 125
Ser Pro Gly Thr Pro Gly Thr Pro Glu Leu Arg Pro Thr Phe Ser Pro
130                 135                 140
Ala Phe Ser Arg Pro Ser Ala Phe Ser Ser Leu Ala Glu Ala Ser Asp
145                 150                 155                 160
Pro Gly Pro Pro Arg Ala Ser Leu Arg Ala Lys Thr Ser Pro Glu Gly
                165                 170                 175
Ala Arg Asp Leu Leu Gly Pro Lys Ala Leu Pro Gly Ser Ser Gln Pro
            180                 185                 190
Arg Gln Tyr Asn Asn Pro Ile Gly Leu Tyr Ser Ala Glu Thr Leu Arg
            195                 200                 205
Glu Met Ala Gln Met Tyr Gln Met Ser Leu Arg Gly Lys Ala Ser Gly
            210                 215                 220
Val Gly Leu Pro Gly Ser Leu Pro Ile Lys Asp Leu Ala Val Asp
225                 230                 235                 240
Ser Ala Ser Pro Val Tyr Gln Ala Val Ile Lys Ser Gln Asn Lys Pro
                245                 250                 255
Glu Asp Glu Ala Asp Glu Trp Ala Arg Arg Ser Ser Asn Leu Gln Ser
            260                 265                 270
Arg Ser Phe Arg Ile Leu Ala Gln Met Thr Gly Thr Glu Phe Met Gln
            275                 280                 285
Asp Pro Asp Glu Glu Ala Leu Arg Arg Ser Ser Thr Pro Ile Glu His
            290                 295                 300
Ala Pro Val Cys Thr Ser Gln Ala Thr Thr Pro Leu Leu Pro Ala Ser
305                 310                 315                 320
Ala Gln Pro Pro Ala Ala Ala Ser Pro Ser Ala Ala Ser Pro Pro Leu
                325                 330                 335
Ala Thr Ala Ala Ala His Thr Ala Ile Ala Ser Ala Ser Thr Thr Ala
            340                 345                 350
Pro Ala Ser Ser Pro Ala Asp Ser Pro Arg Pro Gln Ala Ser Ser Tyr
            355                 360                 365
Ser Pro Ala Val Ala Ala Ser Ser Ala Pro Ala Thr His Thr Ser Tyr
370                 375                 380
Ser Glu Gly Pro Ala Ala Pro Ala Pro Lys Pro Arg Val Val Thr Thr
385                 390                 395                 400
Ala Ser Ile Arg Pro Ser Val Tyr Gln Pro Val Pro Ala Ser Thr Tyr
                405                 410                 415
Ser Pro Ser Pro Gly Ala Asn Tyr Ser Pro Thr Pro Tyr Thr Pro Ser
            420                 425                 430
Pro Ala Pro Ala Tyr Thr Pro Ser Pro Ala Pro Ala Tyr Thr Pro Ser
            435                 440                 445
Pro Val Pro Thr Tyr Thr Pro Ser Pro Ala Pro Ala Tyr Thr Pro Ser
            450                 455                 460
Pro Ala Pro Asn Tyr Asn Pro Ala Pro Ser Val Ala Tyr Ser Gly Gly
465                 470                 475                 480
Pro Ala Glu Pro Ala Ser Arg Pro Pro Trp Val Thr Asp Asp Ser Phe
                485                 490                 495
Ser Gln Lys Phe Ala Pro Gly Lys Ser Thr Thr Ser Ile Ser Lys Gln
            500                 505                 510
Thr Leu Pro Arg Gly Gly Pro Ala Tyr Thr Pro Ala Gly Pro Gln Val
            515                 520                 525
```

```
Pro Pro Leu Ala Arg Gly Thr Val Gln Arg Ala Glu Arg Phe Pro Ala
    530             535                 540

Ser Ser Arg Thr Pro Leu Cys Gly His Cys Asn Asn Val Ile Arg Gly
545             550                 555                 560

Pro Phe Leu Val Ala Met Gly Arg Ser Trp His Pro Glu Glu Phe Thr
                565                 570                 575

Cys Ala Tyr Cys Lys Thr Ser Leu Ala Asp Val Cys Phe Val Glu Glu
            580                 585                 590

Gln Asn Asn Val Tyr Cys Glu Arg Cys Tyr Glu Gln Phe Phe Ala Pro
        595                 600                 605

Leu Cys Ala Lys Cys Asn Thr Lys Ile Met Gly Glu Val Met His Ala
    610                 615                 620

Leu Arg Gln Thr Trp His Thr Thr Cys Phe Val Cys Ala Ala Cys Lys
625                 630                 635                 640

Lys Pro Phe Gly Asn Ser Leu Phe His Met Glu Asp Gly Glu Pro Tyr
                645                 650                 655

Cys Glu Lys Asp Tyr Ile Asn Leu Phe Ser Thr Lys Cys His Gly Cys
            660                 665                 670

Asp Phe Pro Val Glu Ala Gly Asp Lys Phe Ile Glu Ala Leu Gly His
        675                 680                 685

Thr Trp His Asp Thr Cys Phe Ile Cys Ala Val Cys His Val Asn Leu
    690                 695                 700

Glu Gly Gln Pro Phe Tyr Ser Lys Lys Asp Arg Pro Leu Cys Lys Lys
705                 710                 715                 720

His Ala His Thr Ile Asn Leu
                725

<210> SEQ ID NO 5
<211> LENGTH: 3900
<212> TYPE: DNA
<213> ORGANISM: Homo sapiens
<220> FEATURE:
<221> NAME/KEY: CDS
<222> LOCATION: (33)..(3851)

<400> SEQUENCE: 5
cctgcttcgt gcctggtgtg acgtctctca gg atg cct gag ccg ggg aag aag        53
                                    Met Pro Glu Pro Gly Lys Lys
                                    1               5 cca gtc tca gct ttt agc aag aag cca cgg tca gtg gaa gtg gcc gca       101
Pro Val Ser Ala Phe Ser Lys Lys Pro Arg Ser Val Glu Val Ala Ala
        10                  15                  20 ggc agc cct gcc gtg ttc gag gcc gag aca gag cgg gca gga gtg aag       149
Gly Ser Pro Ala Val Phe Glu Ala Glu Thr Glu Arg Ala Gly Val Lys
    25                  30                  35 gtg cgc tgg cag cgc gga ggc agt gac atc agc gcc agc aac aag tac       197
Val Arg Trp Gln Arg Gly Gly Ser Asp Ile Ser Ala Ser Asn Lys Tyr
40                  45                  50                  55 ggc ctg gcc aca gag ggc aca cgg cat acg ctg aca gtg cgg gaa gtg       245
Gly Leu Ala Thr Glu Gly Thr Arg His Thr Leu Thr Val Arg Glu Val
                60                  65                  70 ggc cct gcc gac cag gga tct tac gca gtc att gct ggc tcc tcc aag       293
Gly Pro Ala Asp Gln Gly Ser Tyr Ala Val Ile Ala Gly Ser Ser Lys
            75                  80                  85 gtc aag ttc gac ctc aag gtc ata gag gca gag aag gca gag ccc atg       341
Val Lys Phe Asp Leu Lys Val Ile Glu Ala Glu Lys Ala Glu Pro Met
        90                  95                  100
```

```
ctg gcc cct gcc cct gcc cct gct gag gcc act gga gcc cct gga gaa        389
Leu Ala Pro Ala Pro Ala Pro Ala Glu Ala Thr Gly Ala Pro Gly Glu
    105             110                 115 gcc ccg gcc cca gcc gct gag ctg gga gaa agt gcc cca agt ccc aaa        437
Ala Pro Ala Pro Ala Ala Glu Leu Gly Glu Ser Ala Pro Ser Pro Lys
120             125                 130                 135 ggg tca agc tca gca gct ctc aat ggt cct acc cct gga gcc ccc gat        485
Gly Ser Ser Ser Ala Ala Leu Asn Gly Pro Thr Pro Gly Ala Pro Asp
                140                 145                 150 gac ccc att ggc ctc ttc gtg atg cgg cca cag gat ggc gag gtg acc        533
Asp Pro Ile Gly Leu Phe Val Met Arg Pro Gln Asp Gly Glu Val Thr
            155                 160                 165 gtg ggt ggc agc atc acc ttc tca gcc cgc gtg gcc ggc gcc agc ctc        581
Val Gly Gly Ser Ile Thr Phe Ser Ala Arg Val Ala Gly Ala Ser Leu
        170                 175                 180 ctg aag ccg cct gtg gtc aag tgg ttc aag ggc aaa tgg gtg gac ctg        629
Leu Lys Pro Pro Val Val Lys Trp Phe Lys Gly Lys Trp Val Asp Leu
    185                 190                 195 agc agc aag gtg ggc cag cac ctg cag ctg cac gac agc tac gac cgc        677
Ser Ser Lys Val Gly Gln His Leu Gln Leu His Asp Ser Tyr Asp Arg
200                 205                 210                 215 gcc agc aag gtc tat ctg ttc gag ctg cac atc acc gat gcc cag cct        725
Ala Ser Lys Val Tyr Leu Phe Glu Leu His Ile Thr Asp Ala Gln Pro
                220                 225                 230 gcc ttc act ggc agc tac cgc tgt gag gtg tcc acc aag gac aaa ttt        773
Ala Phe Thr Gly Ser Tyr Arg Cys Glu Val Ser Thr Lys Asp Lys Phe
            235                 240                 245 gac tgc tcc aac ttc aat ctc act gtc cac gag gcc atg ggc acc gga        821
Asp Cys Ser Asn Phe Asn Leu Thr Val His Glu Ala Met Gly Thr Gly
        250                 255                 260 gac ctg gac ctc cta tca gcc ttc cgc cgc acg agc ctg gct gga ggt        869
Asp Leu Asp Leu Leu Ser Ala Phe Arg Arg Thr Ser Leu Ala Gly Gly
    265                 270                 275 ggt cgg cgg atc agt gat agc cat gag gac act ggg att ctg gac ttc        917
Gly Arg Arg Ile Ser Asp Ser His Glu Asp Thr Gly Ile Leu Asp Phe
280                 285                 290                 295 agc tca ctg ctg aaa aag agc agc agt ttc cgg acc ccg agg gac tcg        965
Ser Ser Leu Leu Lys Lys Ser Ser Ser Phe Arg Thr Pro Arg Asp Ser
                300                 305                 310 aag ctg gag gca cca gca gag gag gac gtg tgg gag atc cta cgg cag       1013
Lys Leu Glu Ala Pro Ala Glu Glu Asp Val Trp Glu Ile Leu Arg Gln
            315                 320                 325 gca ccc cca tct gag tac gag cgc atc gcc ttc cag tac ggc gtc act       1061
Ala Pro Pro Ser Glu Tyr Glu Arg Ile Ala Phe Gln Tyr Gly Val Thr
        330                 335                 340 gac ctg cgc ggc atg cta aag agg ctc aag ggc atg agg cgc gat gag       1109
Asp Leu Arg Gly Met Leu Lys Arg Leu Lys Gly Met Arg Arg Asp Glu
    345                 350                 355 aag aag agc aca gcc ttt cag aag aag ctg gag ccg gcc tac cag gtg       1157
Lys Lys Ser Thr Ala Phe Gln Lys Lys Leu Glu Pro Ala Tyr Gln Val
360                 365                 370                 375 agc aaa ggc cac aag atc cgg ctg acc gtg gaa ctg gct gac cat gac       1205
Ser Lys Gly His Lys Ile Arg Leu Thr Val Glu Leu Ala Asp His Asp
                380                 385                 390 gct gag gtc aaa tgg ctc aag aat ggc cag gag atc cag atg agc ggc       1253
Ala Glu Val Lys Trp Leu Lys Asn Gly Gln Glu Ile Gln Met Ser Gly
            395                 400                 405 agg tac atc ttt gag tcc atc ggt gcc aag cgt acc ctg acc atc agc       1301
Arg Tyr Ile Phe Glu Ser Ile Gly Ala Lys Arg Thr Leu Thr Ile Ser
        410                 415                 420
```

|  |  |
|---|---|
| cag tgc tca ttg gcg gac gac gca gcc tac cag tgc gtg gtg ggt ggc<br>Gln Cys Ser Leu Ala Asp Asp Ala Ala Tyr Gln Cys Val Val Gly Gly<br>425                          430                         435 | 1349 |
| gag aag tgt agc acg gag ctc ttt gtg aaa gag ccc cct gtg ctc atc<br>Glu Lys Cys Ser Thr Glu Leu Phe Val Lys Glu Pro Pro Val Leu Ile<br>440                       445                      450                    455 | 1397 |
| acg cgc ccc ttg gag gac cag ctg gtg atg gtg ggg cag cgg gtg gag<br>Thr Arg Pro Leu Glu Asp Gln Leu Val Met Val Gly Gln Arg Val Glu<br>                    460                     465                     470 | 1445 |
| ttt gag tgt gaa gta tcg gag gag ggg gcg caa gtc aaa tgg ctg aag<br>Phe Glu Cys Glu Val Ser Glu Glu Gly Ala Gln Val Lys Trp Leu Lys<br>              475                     480                    485 | 1493 |
| gac ggg gtg gag ctg acc cgg gag gag acc ttc aaa tac cgg ttc aag<br>Asp Gly Val Glu Leu Thr Arg Glu Glu Thr Phe Lys Tyr Arg Phe Lys<br>490                         495                      500 | 1541 |
| aag gac ggg cag aga cac cac ctg atc atc aac gag gcc atg ctg gag<br>Lys Asp Gly Gln Arg His His Leu Ile Ile Asn Glu Ala Met Leu Glu<br>         505                     510                    515 | 1589 |
| gac gcg ggg cac tat gca ctg tgc act agc ggg ggc cag gcg ctg gct<br>Asp Ala Gly His Tyr Ala Leu Cys Thr Ser Gly Gly Gln Ala Leu Ala<br>520                         525                    530                  535 | 1637 |
| gag ctc att gtg cag gaa aag aag ctg gag gtg tac cag agc atc gca<br>Glu Leu Ile Val Gln Glu Lys Lys Leu Glu Val Tyr Gln Ser Ile Ala<br>              540                    545                    550 | 1685 |
| gac ctg atg gtg ggc gca aag gac cag gcg gtg ttc aaa tgt gag gtc<br>Asp Leu Met Val Gly Ala Lys Asp Gln Ala Val Phe Lys Cys Glu Val<br>                   555                     560                   565 | 1733 |
| tca gat gag aat gtt cgg ggt gtg tgg ctg aag aat ggg aag gag ctg<br>Ser Asp Glu Asn Val Arg Gly Val Trp Leu Lys Asn Gly Lys Glu Leu<br>         570                     575                    580 | 1781 |
| gtg ccc gac agc cgc ata aag gtg tcc cac atc ggg cgg gtc cac aaa<br>Val Pro Asp Ser Arg Ile Lys Val Ser His Ile Gly Arg Val His Lys<br>585                         590                     595 | 1829 |
| ctg acc att gac gac gtc aca cct gcc gac gag gct gac tac agc ttt<br>Leu Thr Ile Asp Asp Val Thr Pro Ala Asp Glu Ala Asp Tyr Ser Phe<br>600                         605                    610                    615 | 1877 |
| gtg ccc gag ggc ttc gcc tgc aac ctg tca gcc aag ctc cac ttc atg<br>Val Pro Glu Gly Phe Ala Cys Asn Leu Ser Ala Lys Leu His Phe Met<br>              620                    625                    630 | 1925 |
| gag gtc aag att gac ttc gta ccc agg cag gaa cct ccc aag atc cac<br>Glu Val Lys Ile Asp Phe Val Pro Arg Gln Glu Pro Pro Lys Ile His<br>                   635                     640                   645 | 1973 |
| ctg gac tgc cca ggc cgc ata cca gac acc att gtg gtt gta gct gga<br>Leu Asp Cys Pro Gly Arg Ile Pro Asp Thr Ile Val Val Val Ala Gly<br>         650                     655                    660 | 2021 |
| aat aag cta cgt ctg gac gtc cct atc tct ggg gac cct gct ccc act<br>Asn Lys Leu Arg Leu Asp Val Pro Ile Ser Gly Asp Pro Ala Pro Thr<br>665                         670                    675 | 2069 |
| gtg atc tgg cag aag gct atc acg cag ggg aat aag gcc cca gcc agg<br>Val Ile Trp Gln Lys Ala Ile Thr Gln Gly Asn Lys Ala Pro Ala Arg<br>680                         685                    690                    695 | 2117 |
| cca gcc cca gat gcc cca gag gac aca ggt gac agc gat gag tgg gtg<br>Pro Ala Pro Asp Ala Pro Glu Asp Thr Gly Asp Ser Asp Glu Trp Val<br>                      700                     705                    710 | 2165 |
| ttt gac aag aag ctg ctg tgt gag acc gag ggc cgg gtc cgc gtg gag<br>Phe Asp Lys Lys Leu Leu Cys Glu Thr Glu Gly Arg Val Arg Val Glu<br>              715                    720                    725 | 2213 |
| acc acc aag gac cgc agc atc ttc acg gtc gag ggg gca gag aag gaa<br>Thr Thr Lys Asp Arg Ser Ile Phe Thr Val Glu Gly Ala Glu Lys Glu | 2261 |

-continued

```
                730                 735                 740
gat gag ggc gtc tac acg gtc aca gtg aag aac cct gtg ggc gag gac    2309
Asp Glu Gly Val Tyr Thr Val Thr Val Lys Asn Pro Val Gly Glu Asp
    745                 750                 755 cag gtc aac ctc aca gtc aag gtc atc gac gtg cca gac gca cct gcg    2357
Gln Val Asn Leu Thr Val Lys Val Ile Asp Val Pro Asp Ala Pro Ala
760                 765                 770                 775 gcc ccc aag atc agc aac gtg gga gag gac tcc tgc aca gta cag tgg    2405
Ala Pro Lys Ile Ser Asn Val Gly Glu Asp Ser Cys Thr Val Gln Trp
                780                 785                 790 gag ccg cct gcc tac gat ggc ggg cag ccc atc ctg ggc tac atc ctg    2453
Glu Pro Pro Ala Tyr Asp Gly Gly Gln Pro Ile Leu Gly Tyr Ile Leu
            795                 800                 805 gag cgc aag aag aag aag agc tac cgg tgg atg cgg ctg aac ttc gac    2501
Glu Arg Lys Lys Lys Lys Ser Tyr Arg Trp Met Arg Leu Asn Phe Asp
        810                 815                 820 ctg att cag gag ctg agt cat gaa gcg cgg cgc atg atc gag ggc gtg    2549
Leu Ile Gln Glu Leu Ser His Glu Ala Arg Arg Met Ile Glu Gly Val
    825                 830                 835 gtg tac gag atg cgc gtc tac gcg gtc aac gcc atc ggc atg tcc agg    2597
Val Tyr Glu Met Arg Val Tyr Ala Val Asn Ala Ile Gly Met Ser Arg
840                 845                 850                 855 ccc agc cct gcc tcc cag ccc ttc atg cct atc ggt ccc ccc agc gaa    2645
Pro Ser Pro Ala Ser Gln Pro Phe Met Pro Ile Gly Pro Pro Ser Glu
                860                 865                 870 ccc acc cac ctg gca gta gag gac gtc tct gac acc acg gtc tcc ctc    2693
Pro Thr His Leu Ala Val Glu Asp Val Ser Asp Thr Thr Val Ser Leu
            875                 880                 885 aag tgg cgg ccc cca gag cgc gtg gga gca gga ggc ctg gat ggc tac    2741
Lys Trp Arg Pro Pro Glu Arg Val Gly Ala Gly Gly Leu Asp Gly Tyr
        890                 895                 900 agc gtg gag tac tgc cca gag ggc tgc tca gag tgg gtg gct gcc ctg    2789
Ser Val Glu Tyr Cys Pro Glu Gly Cys Ser Glu Trp Val Ala Ala Leu
    905                 910                 915 cag ggg ctg aca gag cac aca tcg ata ctg gtg aag gac ctg ccc acg    2837
Gln Gly Leu Thr Glu His Thr Ser Ile Leu Val Lys Asp Leu Pro Thr
920                 925                 930                 935 ggg gcc cgg ctg ctt ttc cga gtg cgg gca cac aat atg gca ggg cct    2885
Gly Ala Arg Leu Leu Phe Arg Val Arg Ala His Asn Met Ala Gly Pro
                940                 945                 950 gga gcc cct gtt acc acc acg gag ccg gtg aca gtg cag gag atc ctg    2933
Gly Ala Pro Val Thr Thr Thr Glu Pro Val Thr Val Gln Glu Ile Leu
            955                 960                 965 caa cgg cca cgg ctt cag ctg ccc agg cac ctg cgc cag acc att cag    2981
Gln Arg Pro Arg Leu Gln Leu Pro Arg His Leu Arg Gln Thr Ile Gln
        970                 975                 980 aag aag gtc ggg gag cct gtg aac ctt ctc atc cct ttc cag ggc aag    3029
Lys Lys Val Gly Glu Pro Val Asn Leu Leu Ile Pro Phe Gln Gly Lys
    985                 990                 995 ccc cgg cct cag gtg acc tgg acc aaa gag ggg cag ccc ctg gca ggc    3077
Pro Arg Pro Gln Val Thr Trp Thr Lys Glu Gly Gln Pro Leu Ala Gly
1000                1005                1010                1015 gag gag gtg agc atc cgc aac agc ccc aca gac acc atc ctg ttc atc    3125
Glu Glu Val Ser Ile Arg Asn Ser Pro Thr Asp Thr Ile Leu Phe Ile
                1020                1025                1030 cgg gcc gct cgc cgc gtg cat tca ggc act tac cag gtg acg gtg cgc    3173
Arg Ala Ala Arg Arg Val His Ser Gly Thr Tyr Gln Val Thr Val Arg
            1035                1040                1045 att gag aac atg gag gac aag gcc acg ctg gtg ctg cag gtt gtt gac    3221
```

```
Ile Glu Asn Met Glu Asp Lys Ala Thr Leu Val Leu Gln Val Val Asp
    1050                1055                1060 aag cca agt cct ccc cag gat ctc cgg gtg act gac gcc tgg ggt ctt      3269
Lys Pro Ser Pro Pro Gln Asp Leu Arg Val Thr Asp Ala Trp Gly Leu
    1065                1070                1075 aat gtg gct ctg gag tgg aag cca ccc cag gat gtc ggc aac acg gag      3317
Asn Val Ala Leu Glu Trp Lys Pro Pro Gln Asp Val Gly Asn Thr Glu
1080                1085                1090                1095 ctc tgg ggg tac aca gtg cag aaa gcc gac aag aag acc atg gag tgg      3365
Leu Trp Gly Tyr Thr Val Gln Lys Ala Asp Lys Lys Thr Met Glu Trp
                1100                1105                1110 ttc acc gtc ttg gag cat tac cgc cgc acc cac tgc gtg gtg cca gag      3413
Phe Thr Val Leu Glu His Tyr Arg Arg Thr His Cys Val Val Pro Glu
            1115                1120                1125 ctc atc att ggc aat ggc tac tac ttc cgc gtc ttc agc cag aat atg      3461
Leu Ile Ile Gly Asn Gly Tyr Tyr Phe Arg Val Phe Ser Gln Asn Met
        1130                1135                1140 gtt ggc ttt agt gac aga gcg gcc acc acc aag gag ccc gtc ttt atc      3509
Val Gly Phe Ser Asp Arg Ala Ala Thr Thr Lys Glu Pro Val Phe Ile
    1145                1150                1155 ccc aga cca ggc atc acc tat gag cca ccc aac tat aag gcc ctg gac      3557
Pro Arg Pro Gly Ile Thr Tyr Glu Pro Pro Asn Tyr Lys Ala Leu Asp
1160                1165                1170                1175 ttc tcc gag gcc cca agc ttc acc cag ccc ctg gtg aac cgc tcg gtc      3605
Phe Ser Glu Ala Pro Ser Phe Thr Gln Pro Leu Val Asn Arg Ser Val
                1180                1185                1190 atc gcg ggc tac act gct atg ctc tgc tgt gct gtc cgg ggt agc ccc      3653
Ile Ala Gly Tyr Thr Ala Met Leu Cys Cys Ala Val Arg Gly Ser Pro
            1195                1200                1205 aag ccc aag att tcc tgg ttc aag aat ggc ctg gac ctg gga gaa gac      3701
Lys Pro Lys Ile Ser Trp Phe Lys Asn Gly Leu Asp Leu Gly Glu Asp
        1210                1215                1220 gcc cgc ttc cgc atg ttc agc aag cag gga gtg ttg act ctg gag att      3749
Ala Arg Phe Arg Met Phe Ser Lys Gln Gly Val Leu Thr Leu Glu Ile
    1225                1230                1235 aga aag ccc tgc ccc ttt gac ggg ggc atc tat gtc tgc agg gcc acc      3797
Arg Lys Pro Cys Pro Phe Asp Gly Gly Ile Tyr Val Cys Arg Ala Thr
1240                1245                1250                1255 aac tta cag ggc gag gca cgg tgt gag tgc cgc ctg gag gtg cga gtg      3845
Asn Leu Gln Gly Glu Ala Arg Cys Glu Cys Arg Leu Glu Val Arg Val
                1260                1265                1270 cct cag tgaccaggct ggctcctggg gatggccagg tacaaccgga tgccagccc        3900
Pro Gln <210> SEQ ID NO 6
<211> LENGTH: 1273
<212> TYPE: PRT
<213> ORGANISM: Homo sapiens

<400> SEQUENCE: 6

Met Pro Glu Pro Gly Lys Lys Pro Val Ser Ala Phe Ser Lys Lys Pro
1               5                   10                  15

Arg Ser Val Glu Val Ala Ala Gly Ser Pro Ala Val Phe Glu Ala Glu
            20                  25                  30

Thr Glu Arg Ala Gly Val Lys Val Arg Trp Gln Arg Gly Gly Ser Asp
        35                  40                  45

Ile Ser Ala Ser Asn Lys Tyr Gly Leu Ala Thr Glu Gly Thr Arg His
    50                  55                  60

Thr Leu Thr Val Arg Glu Val Gly Pro Ala Asp Gln Gly Ser Tyr Ala
```

```
                65                  70                  75                  80
Val Ile Ala Gly Ser Ser Lys Val Lys Phe Asp Leu Lys Val Ile Glu
                            85                  90                  95

Ala Glu Lys Ala Glu Pro Met Leu Ala Pro Ala Pro Ala Pro Ala Glu
                100                 105                 110

Ala Thr Gly Ala Pro Gly Glu Ala Pro Ala Pro Ala Ala Glu Leu Gly
                115                 120                 125

Glu Ser Ala Pro Ser Pro Lys Gly Ser Ser Ala Ala Leu Asn Gly
        130                 135                 140

Pro Thr Pro Gly Ala Pro Asp Asp Pro Ile Gly Leu Phe Val Met Arg
145                 150                 155                 160

Pro Gln Asp Gly Glu Val Thr Val Gly Gly Ser Ile Thr Phe Ser Ala
                165                 170                 175

Arg Val Ala Gly Ala Ser Leu Leu Lys Pro Val Val Lys Trp Phe
                180                 185                 190

Lys Gly Lys Trp Val Asp Leu Ser Ser Lys Val Gly Gln His Leu Gln
                195                 200                 205

Leu His Asp Ser Tyr Asp Arg Ala Ser Lys Val Tyr Leu Phe Glu Leu
        210                 215                 220

His Ile Thr Asp Ala Gln Pro Ala Phe Thr Gly Ser Tyr Arg Cys Glu
225                 230                 235                 240

Val Ser Thr Lys Asp Lys Phe Asp Cys Ser Asn Phe Asn Leu Thr Val
                245                 250                 255

His Glu Ala Met Gly Thr Gly Asp Leu Asp Leu Leu Ser Ala Phe Arg
                260                 265                 270

Arg Thr Ser Leu Ala Gly Gly Gly Arg Arg Ile Ser Asp Ser His Glu
        275                 280                 285

Asp Thr Gly Ile Leu Asp Phe Ser Ser Leu Leu Lys Lys Ser Ser Ser
        290                 295                 300

Phe Arg Thr Pro Arg Asp Ser Lys Leu Glu Ala Pro Ala Glu Glu Asp
305                 310                 315                 320

Val Trp Glu Ile Leu Arg Gln Ala Pro Pro Ser Glu Tyr Glu Arg Ile
                325                 330                 335

Ala Phe Gln Tyr Gly Val Thr Asp Leu Arg Gly Met Leu Lys Arg Leu
                340                 345                 350

Lys Gly Met Arg Arg Asp Glu Lys Lys Ser Thr Ala Phe Gln Lys Lys
        355                 360                 365

Leu Glu Pro Ala Tyr Gln Val Ser Lys Gly His Lys Ile Arg Leu Thr
        370                 375                 380

Val Glu Leu Ala Asp His Asp Ala Glu Val Lys Trp Leu Lys Asn Gly
385                 390                 395                 400

Gln Glu Ile Gln Met Ser Gly Arg Tyr Ile Phe Glu Ser Ile Gly Ala
                405                 410                 415

Lys Arg Thr Leu Thr Ile Ser Gln Cys Ser Leu Ala Asp Asp Ala Ala
                420                 425                 430

Tyr Gln Cys Val Val Gly Gly Glu Lys Cys Ser Thr Glu Leu Phe Val
                435                 440                 445

Lys Glu Pro Pro Val Leu Ile Thr Arg Pro Leu Glu Asp Gln Leu Val
        450                 455                 460

Met Val Gly Gln Arg Val Glu Phe Glu Cys Glu Val Ser Glu Glu Gly
465                 470                 475                 480

Ala Gln Val Lys Trp Leu Lys Asp Gly Val Glu Leu Thr Arg Glu Glu
                485                 490                 495
```

```
Thr Phe Lys Tyr Arg Phe Lys Lys Asp Gly Gln Arg His His Leu Ile
            500                 505                 510

Ile Asn Glu Ala Met Leu Glu Asp Ala Gly His Tyr Ala Leu Cys Thr
            515                 520                 525

Ser Gly Gly Gln Ala Leu Ala Glu Leu Ile Val Gln Glu Lys Lys Leu
            530                 535                 540

Glu Val Tyr Gln Ser Ile Ala Asp Leu Met Val Gly Ala Lys Asp Gln
545                 550                 555                 560

Ala Val Phe Lys Cys Glu Val Ser Asp Glu Asn Val Arg Gly Val Trp
                565                 570                 575

Leu Lys Asn Gly Lys Glu Leu Val Pro Asp Ser Arg Ile Lys Val Ser
            580                 585                 590

His Ile Gly Arg Val His Lys Leu Thr Ile Asp Asp Val Thr Pro Ala
            595                 600                 605

Asp Glu Ala Asp Tyr Ser Phe Val Pro Glu Gly Phe Ala Cys Asn Leu
            610                 615                 620

Ser Ala Lys Leu His Phe Met Glu Val Lys Ile Asp Phe Val Pro Arg
625                 630                 635                 640

Gln Glu Pro Pro Lys Ile His Leu Asp Cys Pro Gly Arg Ile Pro Asp
                645                 650                 655

Thr Ile Val Val Val Ala Gly Asn Lys Leu Arg Leu Asp Val Pro Ile
            660                 665                 670

Ser Gly Asp Pro Ala Pro Thr Val Ile Trp Gln Lys Ala Ile Thr Gln
            675                 680                 685

Gly Asn Lys Ala Pro Ala Arg Pro Ala Pro Asp Ala Pro Glu Asp Thr
            690                 695                 700

Gly Asp Ser Asp Glu Trp Val Phe Asp Lys Lys Leu Leu Cys Glu Thr
705                 710                 715                 720

Glu Gly Arg Val Arg Val Glu Thr Thr Lys Asp Arg Ser Ile Phe Thr
                725                 730                 735

Val Glu Gly Ala Glu Lys Glu Asp Glu Gly Val Tyr Thr Val Thr Val
            740                 745                 750

Lys Asn Pro Val Gly Glu Asp Gln Val Asn Leu Thr Val Lys Val Ile
            755                 760                 765

Asp Val Pro Asp Ala Pro Ala Ala Pro Lys Ile Ser Asn Val Gly Glu
            770                 775                 780

Asp Ser Cys Thr Val Gln Trp Glu Pro Pro Ala Tyr Asp Gly Gly Gln
785                 790                 795                 800

Pro Ile Leu Gly Tyr Ile Leu Glu Arg Lys Lys Lys Ser Tyr Arg
                805                 810                 815

Trp Met Arg Leu Asn Phe Asp Leu Ile Gln Glu Leu Ser His Glu Ala
            820                 825                 830

Arg Arg Met Ile Glu Gly Val Val Tyr Glu Met Arg Val Tyr Ala Val
            835                 840                 845

Asn Ala Ile Gly Met Ser Arg Pro Ser Pro Ala Ser Gln Pro Phe Met
            850                 855                 860

Pro Ile Gly Pro Pro Ser Glu Pro Thr His Leu Ala Val Glu Asp Val
865                 870                 875                 880

Ser Asp Thr Thr Val Ser Leu Lys Trp Arg Pro Pro Glu Arg Val Gly
                885                 890                 895

Ala Gly Gly Leu Asp Gly Tyr Ser Val Glu Tyr Cys Pro Glu Gly Cys
            900                 905                 910
```

-continued

```
Ser Glu Trp Val Ala Ala Leu Gln Gly Leu Thr Glu His Thr Ser Ile
    915                 920                 925

Leu Val Lys Asp Leu Pro Thr Gly Ala Arg Leu Leu Phe Arg Val Arg
930                 935                 940

Ala His Asn Met Ala Gly Pro Gly Ala Pro Val Thr Thr Thr Glu Pro
945                 950                 955                 960

Val Thr Val Gln Glu Ile Leu Gln Arg Pro Arg Leu Gln Leu Pro Arg
                965                 970                 975

His Leu Arg Gln Thr Ile Gln Lys Lys Val Gly Glu Pro Val Asn Leu
            980                 985                 990

Leu Ile Pro Phe Gln Gly Lys Pro Arg Pro Gln Val Thr Trp Thr Lys
        995                 1000                1005

Glu Gly Gln Pro Leu Ala Gly Glu Glu Val Ser Ile Arg Asn Ser Pro
    1010                1015                1020

Thr Asp Thr Ile Leu Phe Ile Arg Ala Ala Arg Arg Val His Ser Gly
1025                1030                1035                1040

Thr Tyr Gln Val Thr Val Arg Ile Glu Asn Met Glu Asp Lys Ala Thr
                1045                1050                1055

Leu Val Leu Gln Val Val Asp Lys Pro Ser Pro Pro Gln Asp Leu Arg
            1060                1065                1070

Val Thr Asp Ala Trp Gly Leu Asn Val Ala Leu Glu Trp Lys Pro Pro
        1075                1080                1085

Gln Asp Val Gly Asn Thr Glu Leu Trp Gly Tyr Thr Val Gln Lys Ala
    1090                1095                1100

Asp Lys Lys Thr Met Glu Trp Phe Thr Val Leu Glu His Tyr Arg Arg
1105                1110                1115                1120

Thr His Cys Val Val Pro Glu Leu Ile Ile Gly Asn Gly Tyr Tyr Phe
                1125                1130                1135

Arg Val Phe Ser Gln Asn Met Val Gly Phe Ser Asp Arg Ala Ala Thr
            1140                1145                1150

Thr Lys Glu Pro Val Phe Ile Pro Arg Pro Gly Ile Thr Tyr Glu Pro
        1155                1160                1165

Pro Asn Tyr Lys Ala Leu Asp Phe Ser Glu Ala Pro Ser Phe Thr Gln
    1170                1175                1180

Pro Leu Val Asn Arg Ser Val Ile Ala Gly Tyr Thr Ala Met Leu Cys
1185                1190                1195                1200

Cys Ala Val Arg Gly Ser Pro Lys Pro Lys Ile Ser Trp Phe Lys Asn
                1205                1210                1215

Gly Leu Asp Leu Gly Glu Asp Ala Arg Phe Arg Met Phe Ser Lys Gln
            1220                1225                1230

Gly Val Leu Thr Leu Glu Ile Arg Lys Pro Cys Pro Phe Asp Gly Gly
        1235                1240                1245

Ile Tyr Val Cys Arg Ala Thr Asn Leu Gln Gly Glu Ala Arg Cys Glu
    1250                1255                1260

Cys Arg Leu Glu Val Arg Val Pro Gln
1265                1270
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7

```
gtgccctctc actcaaccct                                                20
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
acacatgccc tcctccaagc                                                20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
tggcctttcc tcaggaccac                                                20
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
tcctgcacag ttttgtagcc                                                20
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
tgactctggc tctctcttgc t                                              21
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
tccaggaacc agggctgagt                                                20
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggctcgcgct aacacatctg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccacctgtg gagagctgta                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cactccttgc tctcctcacc                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctctatccac gccagacaca                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtaaccgcc acctgttgcc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tccaggaggt ccaacgtgag                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccaccaatgg gcatggagca                                              20

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agcaggactc cctggcttct                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttgctgtgtc tcccgtgagt                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaggtccctt ccatgagtga                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtgaacaca ttccctaacc                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cccagcagag ttatacattg                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctcccttga cctgttgtct                                                   20
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gccctaacta ccttggacac                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ggctgtcctt ctgggtgtaa                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tcttggctct tgtggctcct                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
catttctctg gctaggagtg                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ctgggagaag ctatcatctg                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tgcaccctcg gtggcctaca                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctcccaacca gggctcagac                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gttctgggag ctgccttact                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggaagagaca tgggtcagag                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agtcaagccc gctccctctc                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacatgccat cgaagtgttc                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgatttgggg tttgtcttgg                                              20

<210> SEQ ID NO 38

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctagcgtggc aaggtatgta                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtctcacgca ggtctgttct                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcttcctctc tctccccatt                                              20

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttgggtgacc tgtgcctg                                                18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccctgctccc acacttag                                                18

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cggggtgcac gctccaa                                                 17

<210> SEQ ID NO 44
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccagcagccc aaacctca                                                   18

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gcgggctcat gggtcca                                                    17

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cccagcaaag gcttttga                                                   18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gcctgggtga cagagcaa                                                   18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccttcccacc ccaatgct                                                   18

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tggcgaggtg accgtgg                                                    17

<210> SEQ ID NO 50
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 50
cctctgtgtg ccttgtgc                                                    18

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttgtctcccg cccctg                                                      17

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cccgagccca ggacaga                                                     17

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aagccccttc ccccatctct                                                  20

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccagctgccc caggaac                                                     17

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggtcggccca actgactt                                                    18

<210> SEQ ID NO 56
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 56
agtctctcac cacagcct                                                    18

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atgtgccacc taccctttc                                                   19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gatgagggtg ctgtgctat                                                   19

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59 ccaggggct gcagtct                                                      17

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cctctcctct cctgtgtag                                                   19

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagccacagc cacagtag                                                    18

<210> SEQ ID NO 62
<211> LENGTH: 18
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 62
ggcaggaggc aaggctat                                                    18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgccggtccc tctctctc                                                    18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
caggaaagct gcggacac                                                    18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tccgcagctt tcctgcca                                                    18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctcccctgag gccatctc                                                    18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggggagccaa ccctcatg                                                    18

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 68
caagccctaa agcctcatgt                                                    20

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tcacgccaca cccacaca                                                      18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tccatctcag tctccacct                                                     19

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggctggggta tctggcaag                                                     19

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccgacccacc ctaccctg                                                      18

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctgtcagcca agctccactt c                                                  21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 74
ccttgctctt ccctctgtga g                                              21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tcccgtttct ctgaactaca                                                20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccacacaccc atcttataga                                                20

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agctcctctg ctccctac                                                  18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cggcaccacg taggtaga                                                  18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctctggggtc tgacttgg                                                  18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 80
gctgcccctc tgtgttct                                                    18

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gacgagcaac gttactcaag                                                  20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
accttccctc ggatctgttt                                                  20

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gttccagacc agagctgc                                                    18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ttaactgggg aggggggcg                                                   18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttccccaggc ttgctcag                                                    18

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
```
atggcaaggt gagcatgttc                                               20

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgggagtggg gtgtcagt                                                 18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acctccactg gacaccaa                                                 18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cgggccctca cttagcta                                                 18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccactggatg ggaacaac                                                 18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cattttccag tccactgc                                                 18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ccaggttcag ggttaagc                                                   18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggaggcgtgg tgacccaa                                                   18

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtccacggtg aggacagtg                                                  19

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gaggctctcg gcatcagg                                                   18

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctgttggtga caggacttgg t                                               21

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ctgtgggaac agggagagg                                                  19

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ggagaggact gctcaacgtc                                                 20

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gtgtctccct gggtccct                                                  18

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cgaggacaac ggagcaaag                                                 19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ctttgctccg ttgtcctcg                                                 19

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cgcagcacag gagacacact                                                20

<210> SEQ ID NO 103
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gggcacacgg c                                                         11

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gggggcatct atgtctgc                                                  18

```
<210> SEQ ID NO 105
<211> LENGTH: 14
<212> TYPE: PRT
<213> ORGANISM: Homo sapiens

<400> SEQUENCE: 105

Tyr Glu Gln Phe Phe Ala Leu Leu Cys Ala Lys Cys Asn Thr
 1               5                  10

<210> SEQ ID NO 106
<211> LENGTH: 14
<212> TYPE: PRT
<213> ORGANISM: Homo sapiens

<400> SEQUENCE: 106

Tyr Glu Gln Phe Phe Ala Pro Leu Cys Ala Lys Cys Asn Thr
 1               5                  10

<210> SEQ ID NO 107
<211> LENGTH: 14
<212> TYPE: PRT
<213> ORGANISM: Mus musculus

<400> SEQUENCE: 107

Tyr Glu Gln Phe Phe Ala Pro Ile Cys Ala Lys Cys Asn Thr
 1               5                  10

<210> SEQ ID NO 108
<211> LENGTH: 14
<212> TYPE: PRT
<213> ORGANISM: Rattus norvegicus

<400> SEQUENCE: 108

Tyr Glu Gln Phe Phe Ala Pro Ile Cys Ala Lys Cys Asn Thr
 1               5                  10

<210> SEQ ID NO 109
<211> LENGTH: 14
<212> TYPE: PRT
<213> ORGANISM: Gallus gallus

<400> SEQUENCE: 109

Tyr Glu Gln Phe Phe Ala Pro Thr Cys Ser Arg Cys His Thr
 1               5                  10

<210> SEQ ID NO 110
<211> LENGTH: 14
<212> TYPE: PRT
<213> ORGANISM: Danio rerio

<400> SEQUENCE: 110

Tyr Glu Glu Phe Phe Ala Pro Thr Cys Ala Arg Cys Ser Thr
 1               5                  10

<210> SEQ ID NO 111
<211> LENGTH: 14
<212> TYPE: PRT
<213> ORGANISM: Drosophila melanogaster

<400> SEQUENCE: 111

Phe Glu Lys Tyr Leu Ala Pro Thr Cys Ser Lys Cys Ala Gly
 1               5                  10

<210> SEQ ID NO 112
```

```
<211> LENGTH: 83
<212> TYPE: PRT
<213> ORGANISM: Homo sapiens

<400> SEQUENCE: 112

Leu Cys Gly His Cys Asn Asn Val Ile Arg Gly Pro Phe Leu Val Ala
 1               5                  10                  15

Met Gly Arg Ser Trp His Pro Glu Glu Phe Thr Cys Ala Tyr Cys Lys
                20                  25                  30

Thr Ser Leu Ala Asp Val Cys Phe Val Glu Glu Gln Asn Asn Val Tyr
            35                  40                  45

Cys Glu Arg Cys Tyr Glu Gln Phe Phe Ala Pro Leu Cys Ala Lys Cys
        50                  55                  60

Asn Thr Lys Ile Met Gly Glu Val Met His Ala Leu Arg Gln Thr Trp
65                  70                  75                  80

His Thr Thr

<210> SEQ ID NO 113
<211> LENGTH: 83
<212> TYPE: PRT
<213> ORGANISM: Homo sapiens

<400> SEQUENCE: 113

Leu Cys Gly His Cys Asn Asn Val Ile Arg Gly Pro Phe Leu Val Ala
 1               5                  10                  15

Met Gly Arg Ser Trp His Pro Glu Glu Phe Thr Cys Ala Tyr Cys Lys
                20                  25                  30

Thr Ser Leu Ala Asp Val Cys Phe Val Glu Glu Gln Asn Asn Val Tyr
            35                  40                  45

Cys Glu Arg Cys Tyr Glu Gln Phe Phe Ala Leu Leu Cys Ala Lys Cys
        50                  55                  60

Asn Thr Lys Ile Met Gly Glu Val Met His Ala Leu Arg Gln Thr Trp
65                  70                  75                  80

His Thr Thr
```